United States Patent [19]

Cross et al.

[11] Patent Number: 4,590,200

[45] Date of Patent: May 20, 1986

[54] NAPHTHALENE THROMBOXANE SYNTHETASE INHIBITORS

[75] Inventors: Peter E. Cross, Canterbury; Roger P. Dickinson, Dover, both of England

[73] Assignee: Pfizer Inc., New York, N.Y.

[21] Appl. No.: 663,244

[22] Filed: Oct. 22, 1984

Related U.S. Application Data

[62] Division of Ser. No. 406,140, Aug. 9, 1982, Pat. No. 4,496,572.

[30] Foreign Application Priority Data

Aug. 26, 1981 [GB] United Kingdom ................. 8125976

[51] Int. Cl.[4] ................. C07D 213/06; A61K 31/435
[52] U.S. Cl. ..................... 514/357; 514/277; 514/351; 514/345; 514/355; 514/399; 546/342; 546/333; 546/334; 546/300; 546/301; 546/302; 546/315; 548/335
[58] Field of Search ............... 546/333, 334, 342, 300, 546/301, 302, 315; 548/335; 514/277, 357, 399, 355

[56] References Cited

U.S. PATENT DOCUMENTS

| | | | |
|---|---|---|---|
| 4,179,565 | 12/1979 | Jarque et al. | 546/63 |
| 4,217,357 | 8/1980 | Cross et al. | 424/273 R |
| 4,230,714 | 10/1980 | Cross et al. | 424/263 |
| 4,273,782 | 8/1981 | Cross et al. | 424/273 R |
| 4,410,539 | 10/1983 | Cross et al. | 424/273 R |

FOREIGN PATENT DOCUMENTS 0003560 8/1979 European Pat. Off. .
1333471 10/1983 United Kingdom .

OTHER PUBLICATIONS

John G. Topliss, "Utilization of Operation Schemes for Analog Synthesis in Drug Design", *Journal of Medicinal Chemistry*, vol. 15, No. 10, p. 1006 (1972).

*Primary Examiner*—Jane T. Fan
*Attorney, Agent, or Firm*—Charles J. Knuth; Peter C. Richardson

[57] ABSTRACT

A novel series of carboxy-substituted naphthalenes and carboxy-substituted benzo-fused heterocycles, such as carboxy-substituted derivatives of indole, benzofuran and benzothiophene, has been prepared, including their pharmaceutically acceptable salts. These particular compounds are useful in therapy for the treatment of thrombosis, ischaemic heart disease, stroke, transient ischaemic attack, migraine, peripheral vascular disease, the vascular complications of diabetes and endotoxic shock. Preferred member compounds include 2-(1-imidazolylmethyl)-3-methylbenzo[b]thiophene-5-carboxylic acid and 3-methyl-2-(3-pyridylmethyl)benzo[b]-thiophene-5-carboxylic acid, respectively. Methods for preparing these compounds from known starting materials are provided.

6 Claims, No Drawings

NAPHTHALENE THROMBOXANE SYNTHETASE INHIBITORS

This is a division of application Ser. No. 406,140, filed on Aug. 9, 1982 and now U.S. Pat. No. 4,496,572, issued Jan. 29, 1985.

BACKGROUND OF THE INVENTION

This invention relates to certain naphthalenes and benzo-fused heterocycles, namely benzothiophenes, benzofurans and indoles, which are substituted by a carboxy, lower alkoxycarbonyl or carbamoyl group. Such compounds are able to selectively inhibit the action of the thromboxane synthetase enzyme without significantly inhibiting the action of the prostacyclin synthetase or cyclooxygenase enzymes. The compounds are thus useful as therapeutic agents, for example, in the treatment of thrombosis, ischaemic heart disease, stroke, transient ischaemic attack, migraine, peripheral vascular disease, the vascular complications of diabetes, and endotoxin shock.

SUMMARY OF THE INVENTION

Thus, according to the invention, there are provided compounds of the general formula:

$$Y-\text{"A"}\text{"B"}-R \quad (I)$$

with $R^1$ on ring "B" and $X$ on ring "B"

wherein
$R^1$, which is attached to a carbon atom of ring "B", is hydrogen, halo, $C_1$-$C_4$ alkyl or —S($C_1$-$C_4$ alkyl);
Y, which is attached to ring "A", is —COOH, —COO($C_1$-$C_4$ alkyl) or —CONH$_2$;
X is O, S, NH, N($C_1$-$C_4$ alkyl) or —CH=CH—; and
R, which is attached to a carbon atom of ring "B", is a group of the formula:

$$\text{N} \diagup \text{N}-CH_2- \text{ or } (3\text{-pyridyl})-Z-$$

where Z is —CH$_2$—, —CH=CH—, —OCH$_2$—, —CO— or —S—; and the pharmaceutically acceptable salts thereof.

"Halo" means F, Cl, Br or I. "Halo" is preferably Cl or Br.

Alkyl groups of 3 or 4 carbon atoms may be straight or branched chain.

As stated above, R and $R^1$ are attached to a carbon atom of ring "B". When X is —CH=CH—, it should be understood that this includes the situation where R and/or $R^1$ are attached to a carbon atom of this group, e.g. as —C($R^1$)=C(R)—.

The invention also includes the novel intermediates of the formula:

$$NC-\text{"A"}\text{"B"}-R$$

with $R^1$ on ring "B" and $X$ on ring "B"

where X, R and $R^1$ are as defined for formula (I) and the —CN group is attached to a carbon atom of ring "A".

In one preferred group of compounds:

(a) X is S; R is 1-imidazolylmethyl, 3-pyridyloxymethyl, 3-pyridylmethyl, 3-pyridylthio, 2-(3-pyridyl)-vinyl or nicotinoyl; Y is —COOCH$_3$, —COOC$_2$H$_5$, —COOH or —CONH$_2$ attached to the 5-, 6- or 7-position of ring "A"; and $R^1$ is H, CH$_3$, Cl, Br or —SCH$_3$;

(b) X is O; R is 3-pyridylmethyl or 1-imidazolylmethyl; Y is —COOH or —COOCH$_3$ attached to the 5- or 6-position of ring "A"; $R^1$ is CH$_3$, C$_2$H$_5$, Cl or Br;

(c) X is NH; R is 1-imidazolylmethyl; Y is —COOH or —COOC$_2$H$_5$ attached to the 5-position of ring "A"; and $R^1$ is CH$_3$;

(d) X is N(CH$_3$); R is 1-imidazolylmethyl; Y is —COOH or —COOC$_2$H$_5$ attached to the 5-position of ring "A"; and $R^1$ is CH$_3$; or (e) X is —CH=CH—; R is 1-imidazolylmethyl or 3-pyridylmethyl; Y is —COOH; and $R^1$ is H or CH$_3$.

More preferably:
X is O, S, N ($C_1$-$C_4$ alkyl) or —CH=CH—;
R is $$-CH_2-N\diagup N \text{ or } -CH_2-\text{(3-pyridyl)}$$

and is attached to the 2-position;
Y is —CO$_2$H, which is attached to the 5- or 6-position when X is O,
S or N($C_1$-$C_4$ alkyl), and to the 6- or 7-position when X is —CH=CH—; and
$R^1$ is $C_1$-$C_4$ alkyl, $C_1$-$C_4$ alkylthio, Cl or Br and is attached to the 3-position when X is O, S or $C_1$-$C_4$ alkyl, and to the 1-position when X is —CH=CH—.

The preferred alkyl groups are methyl and ethyl and the preferred alkylthio group is methylthio.

The most preferred compounds are:

[Structure: benzothiophene with HO$_2$C, CH$_3$, and imidazolylmethyl substituents]

[Structure: benzothiophene with HO$_2$C, CH$_3$, and pyridylmethyl substituents]

[Structure: benzothiophene with HO$_2$C, Cl, and imidazolylmethyl substituents]

[Structure: benzothiophene with HO$_2$C, SCH$_3$, and imidazolylmethyl substituents]

[Structure: benzothiophene with HO$_2$C, CH$_3$, and imidazolylmethyl substituents]

-continued

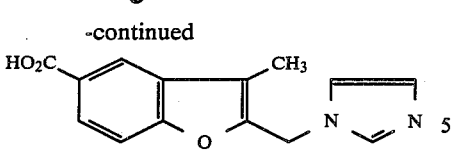

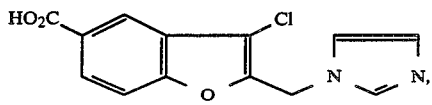

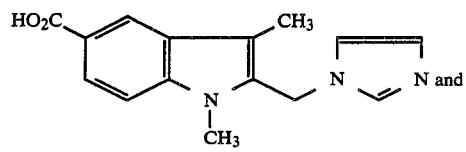

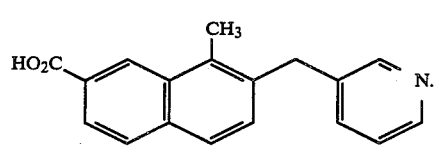

DETAILED DESCRIPTION OF THE INVENTION

The compounds of the formula (I) can be prepared as follows:

(1) The imidazolylmethyl esters of the formula (I) in which X is O, S, N($C_1$-$C_4$ alkyl) or —CH=CH— can be prepared as follows:

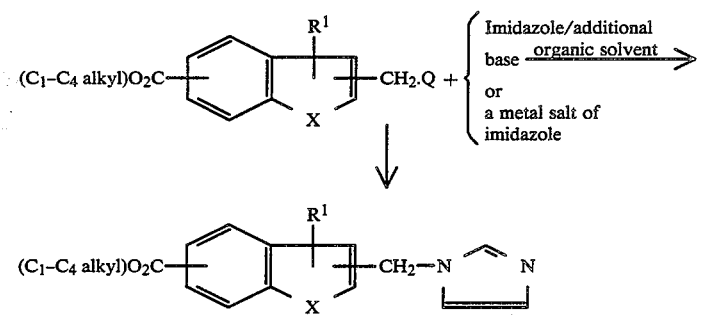

Q is a facile leaving group such as halo, $C_1$-$C_4$ alkylsulphonyloxy or Ar $SO_2O$— where Ar is phenyl optionally substituted by 1 or 2 substituents selected from $C_1$-$C_4$ alkyl, $C_1$-$C_4$ alkoxy and halogen.

The preferred metal salts of imidazole are the alkali metal and the silver salts. The most preferred salt is the sodium salt, preparable from imidazole and sodium hydride.

Q is preferably Cl or Br.

The preferred additional base is $NaHCO_3$ (in this case up to a 10 x excess of imidazole is desirable).

Preferred solvents are DMF (when using NaH) and acetone (when using $NaHCO_3$). Typically the reaction proceeds to completion at room temperature, although in some cases heating, e.g. up to 100° C. and occasionally at reflux, is necessary to accelerate the reaction, which is generally complete in 12 hours or less. The product can be isolated and purified by conventional procedures.

The above process can be carried out using —CN in place of the —COO($C_1$-$C_4$ alkyl) substituent, followed by converting —CN conventionally to —COOH or —$CONH_2$.

(2) Compounds in which Y is —COOH or —$CONH_2$ are obtainable by the hydrolysis of the corresponding nitriles in a conventional manner:

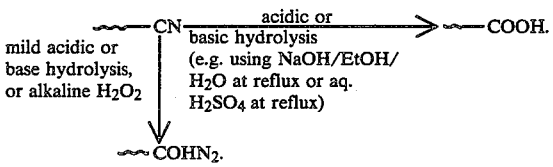

The nitriles are generally obtained by treatment of the corresponding —Br compounds with CuCN/DMF at reflux, e.g. as follows:

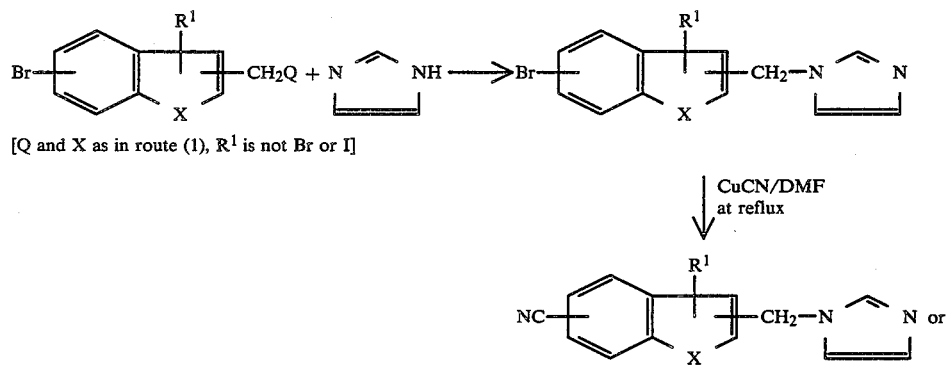

[Q and X as in route (1), $R^1$ is not Br or I]

-continued

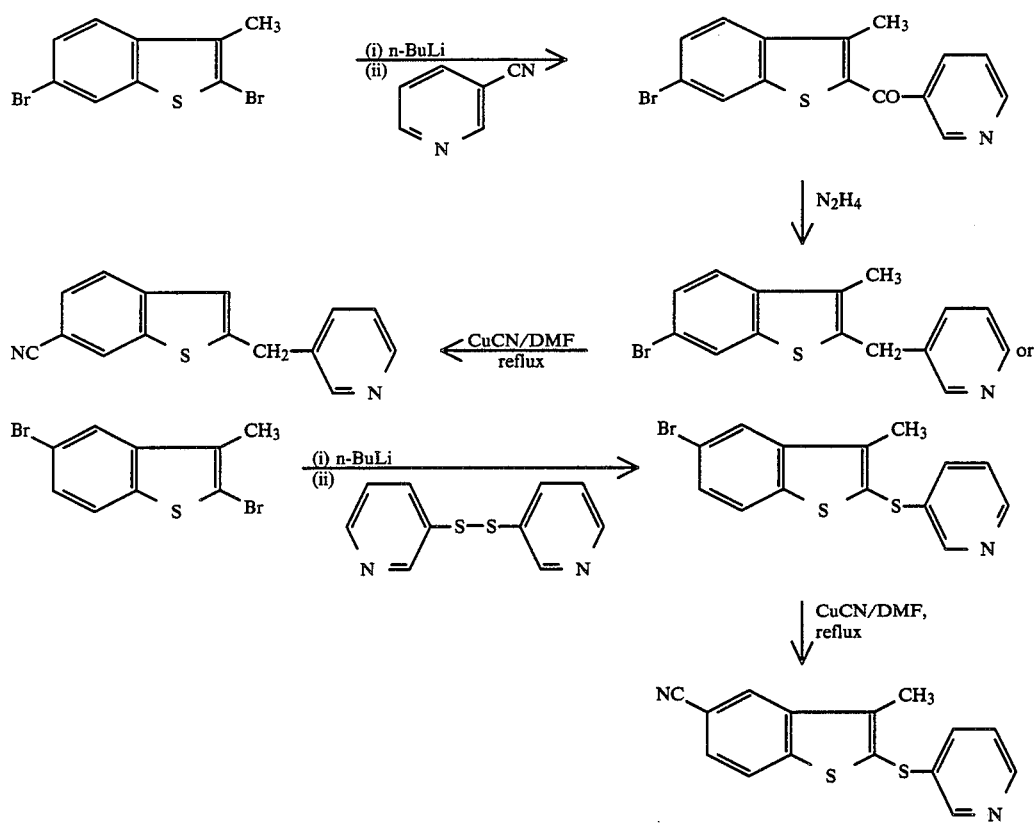

(3) Some of the compounds of the invention can be prepared from other compounds of the invention, e.g. the acids can be prepared by the acidic (e.g. HCl) or basic (e.g. KOH) hydrolysis of the corresponding esters in a conventional manner. Similarly reaction of the esters with ammonia produces the amides, which can also be prepared by reaction of the corresponding acids with carbonyl di-imidazole or thionyl chloride, and then with ammonia.

(4a) The compounds in which X=NH are generally prepared by the hydrolysis of the corresponding —N(-$C_1$-$C_4$ alkanoyl) [preferably N-acetyl] or —N(benzoyl) compounds, e.g. using KOH/aq.MeOH or $NH_3$/EtOH.

For example, for 2-(1-imidazolylmethyl)indoles (X=NH) the following sequence can be used:

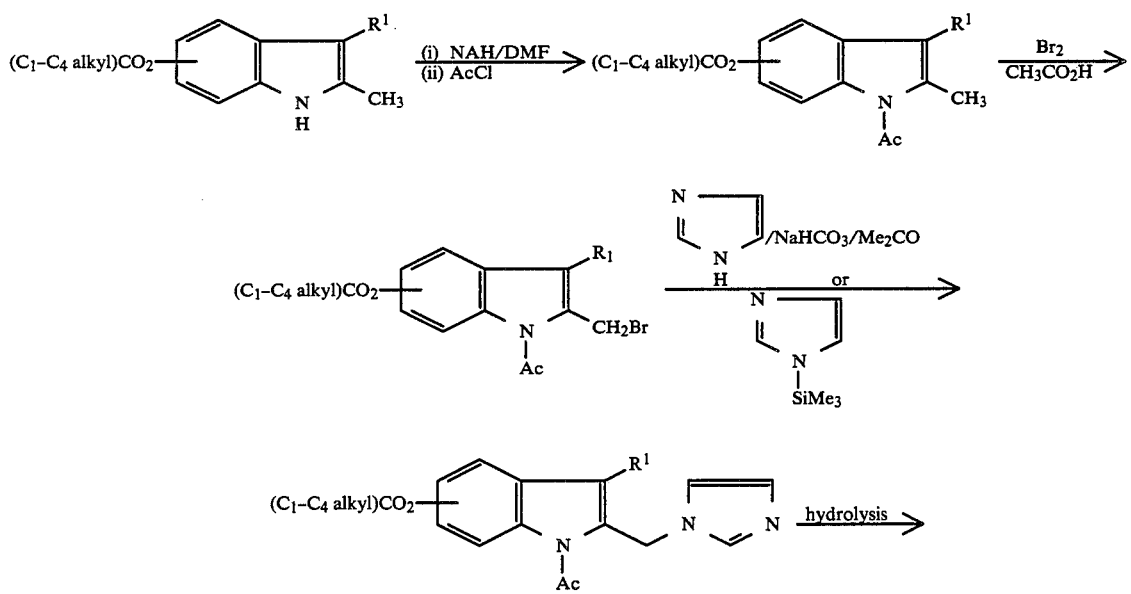

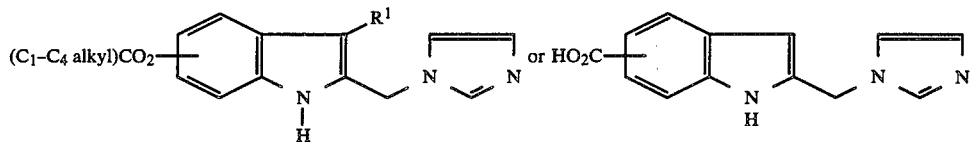

KOH usually hydrolyses both the —N.Ac and ester groups. NH3/EtOH usually just hydrolyses the —N.Ac group.

This reaction can also be carried out using compounds in which the —COO(C1–C4 alkyl) group is replaced by Br or CN. Treatment of the products were R=Br with CuCN gives the corresponding nitriles; the —CN function can be converted by hydrolysis to —CONH2 or —COOH in a conventional manner.

(4b) Compounds in which X is N(C1–C4 alkyl) are most conveniently prepared by alkylation of esters in which X is NH using standard methods, e.g.:

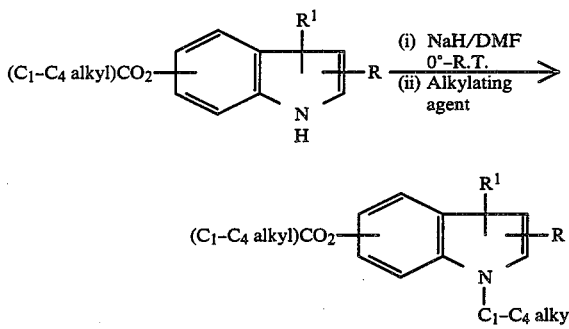

Typical alkylating agents are alkyl halides and dialkyl sulphates.

Again the reaction can be carried out using —Br or —CN in place of —CO2(C1–C4 alkyl), etc., as mentioned in (a) above.

In a typical procedure the indole ester in DMF is stirred with sodium hydride at room temperature (R.T.) for about 30 minutes and then a solution of dimethyl sulphate in DMF is added and the resulting mixture is stirred at room temperature for up to about 24 hours. The product can then be isolated and purified conventionally.

(4c) 3-(1-Imidazolylmethyl)substituted compounds are available by the route:

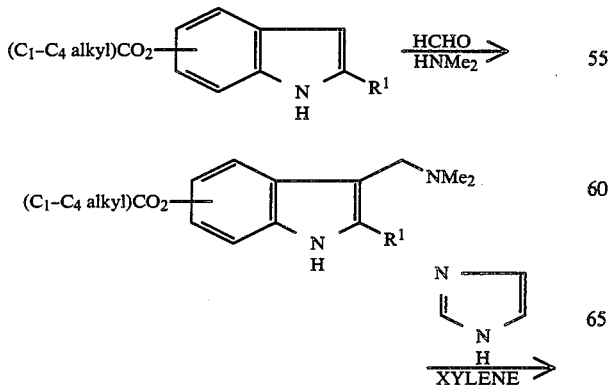

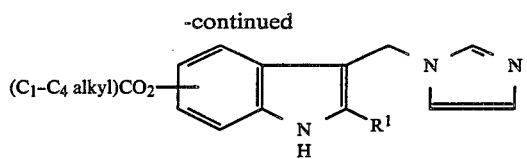

The first stage is the Mannich reaction. It may be carried out conventionally, and, as in (a) and (b) above, starting materials having —Br or —CN can be used, followed by conversion of Br to CN, and hydrolysis of —CN to —COOH conventionally.

(5) Certain imidazolylmethylnaphthalenes are available by elaboration of bromo tetralones:

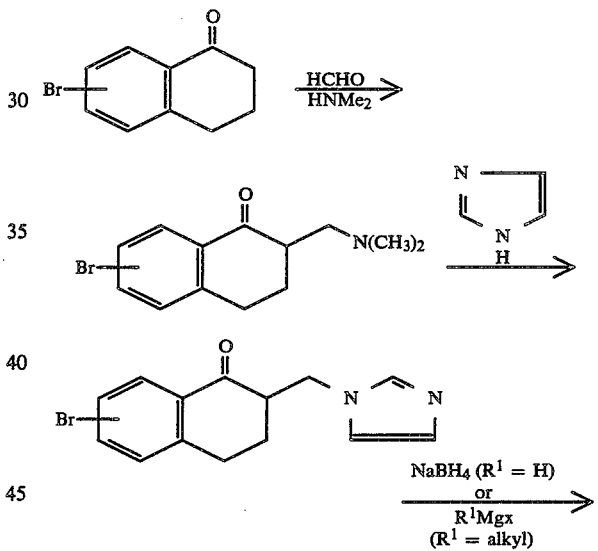

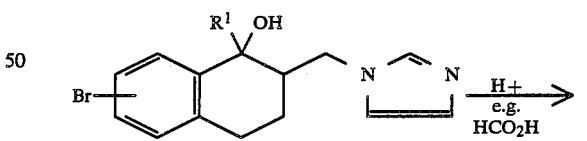

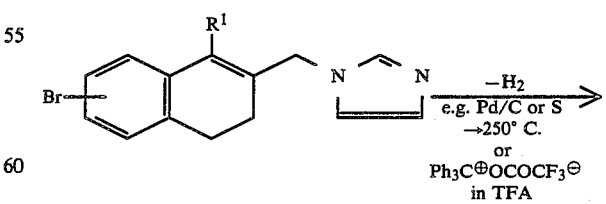

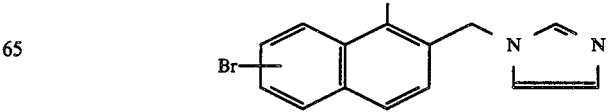

In the case of trityl trifluoroacetate in trifluoroacetic acid the carbinol precursor may also be used as the substrate.

The —Br group may be converted to —CN and then to —CONH$_2$, —COOH or —COO(C$_1$-C$_4$ alkyl) conventionally.

(6) The pyridyloxymethyl compounds can be prepared as follows:

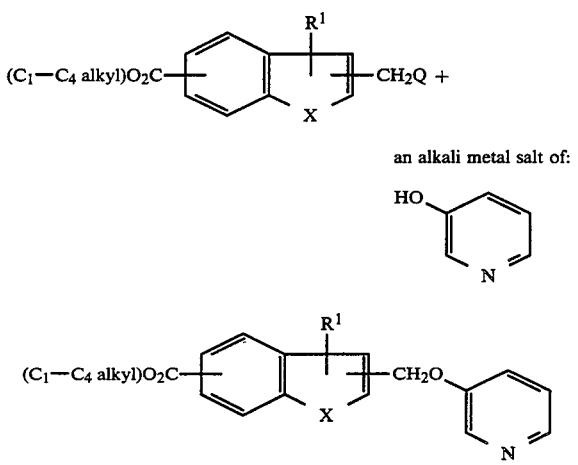

an alkali metal salt of:

Q is as defined in Route (1); X=O, S, N (C$_1$-C$_4$ alkyl) or —CH=CH—. The preferred alkali metal salt is the sodium salt, obtainable from the hydroxypyridine and sodium hydride. Typically the reaction proceeds to completion in a suitable organic solvent (e.g. DMF) at room temperature in 6 hours or less, but heating at up to 100° C. may in some cases be necessary, and again the product can be isolated and purified by conventional procedures.

The above reaction can also be carried out with —Br or —CN in place of —CO$_2$(C$_1$-C$_4$ alkyl), etc., as mentioned in (4a).

(7) The vinyl esters of the formula (I) can be prepared by the Wittig reaction as follows:

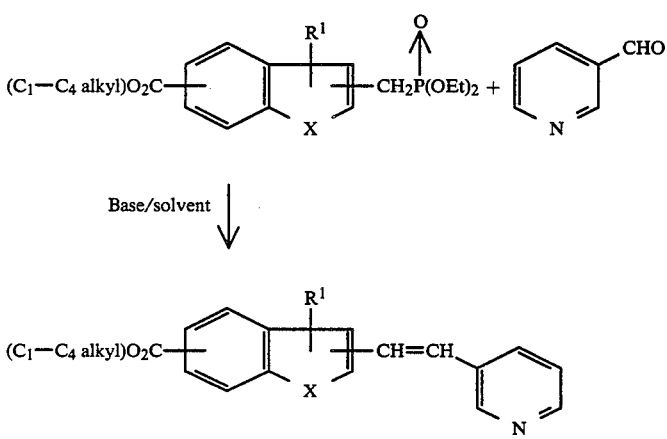

(X=O, S, N [C$_1$-C$_4$ alkyl] or —CH=CH—).

The reaction can generally be carried out by stirring the reaction mixture at room temperature for a few hours, although in some cases heating at up to 100° C. may be necessary, the preferred base/solvent combination being sodium hydride/dimethoxyethane, and again the product can be isolated and pruified by conventional procedures. The reaction is generally complete in 24 hours or less.

As mentioned in (7), starting materials in which —CO$_2$(C$_1$-C$_4$ alkyl) is replaced by —Br or —CN, or in which X is —N(acetyl), etc., can be used.

The phosphorus-containing starting materials are obtainable conventionally, e.g. by the reaction of the corresponding chloromethyl compound with triethyl phosphite under reflux for about 3 hours.

(9) Preparation of certain 3-pyridylmethyl, pyridylthio and 3-pyridylcarbonyl (nicotinoyl) analogues (i) Generally prepared via a pyridyl ketone, e.g.

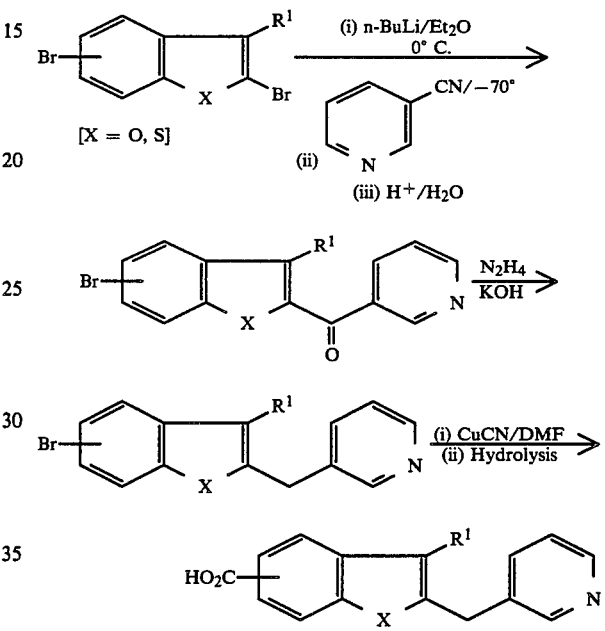

Alternatively the —CN function introduced by the CuCN can be converted to —CONH$_2$.

(ii) In certain cases direct metallation of a compound with a vacant 2-position may be carried out, e.g.

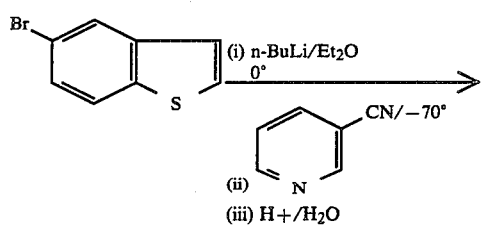

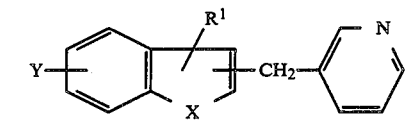

(v) Specific methods exist for particular systems, e.g. for 2-substituted benzofurans:

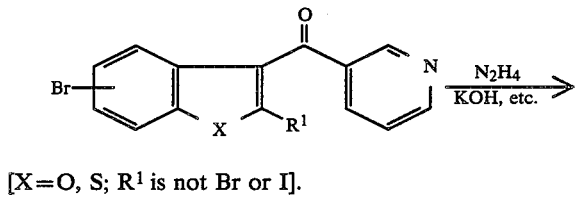

[R$^1$ = H, alkyl]

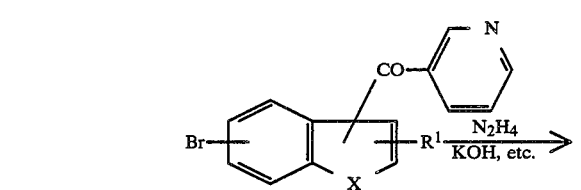

(see Chim. Ther. 2, 113, 1967)

(vi) 2-Nicotinoylindoles may be prepared via metallation of an N-benzenesulphonyl protected indole (see J. Org. Chem. 38, 3324, 1973 and J. Org. Chem. 46, 3857, 1981).

Several 3-substituted isomers may be prepared by an analogous route:

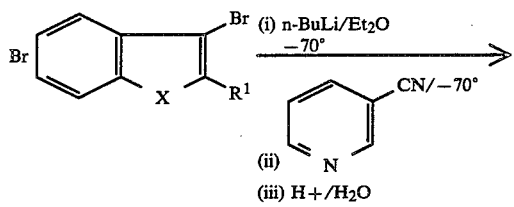

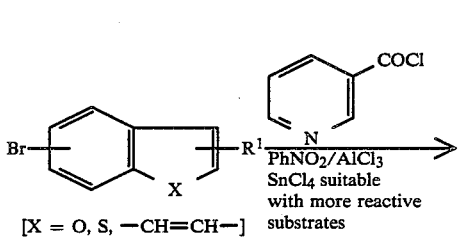

[X=O, S; R$^1$ is not Br or I].

(iii) In many cases, pyridyl ketones may be prepared by Friedel-Crafts acylation using nicotinoyl chloride:

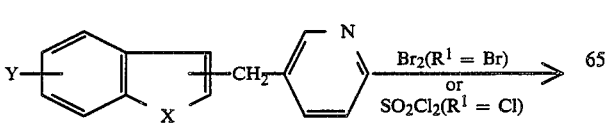

Use of LDA/THF in place of t-BuLi/THF is preferred when R$^1$=Br or I.

(vii) 3-Nicotinoyl ketones may be prepared via an indol Grignard intermediate:

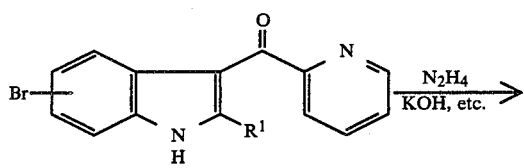

(iv) When R$^1$=Br, Cl, the halogen atom may be introduced by direct halogenation of an intermediate where R$^1$=H:

Alternatively the pyridylmethyl group may be introduced directly via a Grignard intermediate:

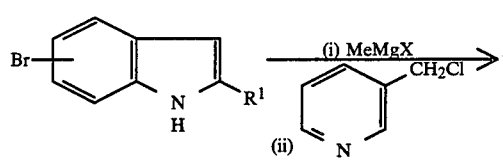

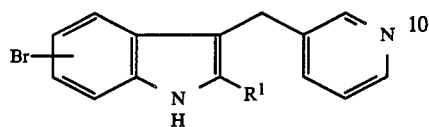

(viii) Certain naphthalene derivatives are available from bromo tetralones, e.g.

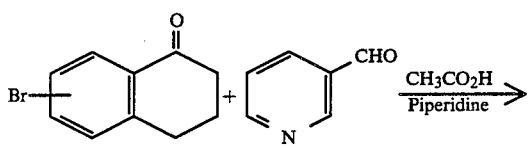

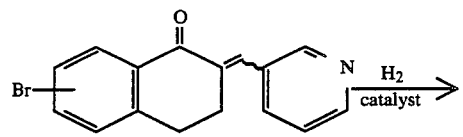

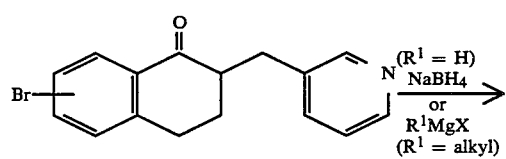

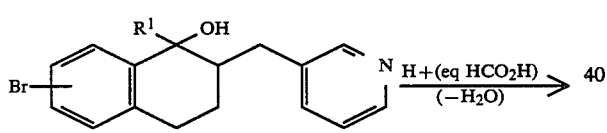

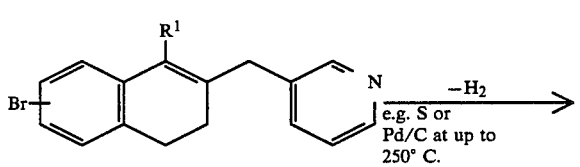

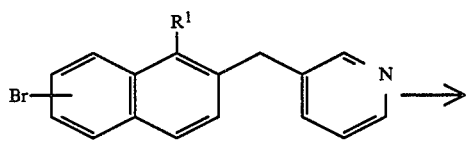

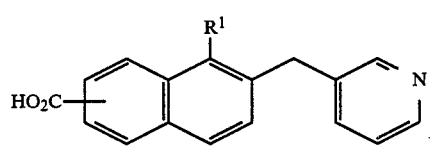

In the case of trityl trifluoroacetate in trifluoroacetic acid the carbinol precursor may also be used as the substrate.

Similar routes are possible from 2-tetralones, e.g.

(ix) Compounds in which Z is CO may be prepared from an appropriate bromo substituted nicotinoyl ketone as shown:

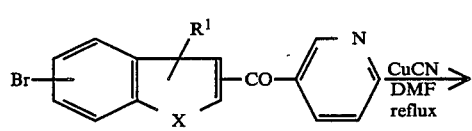

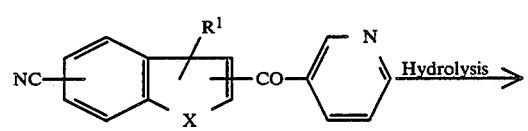

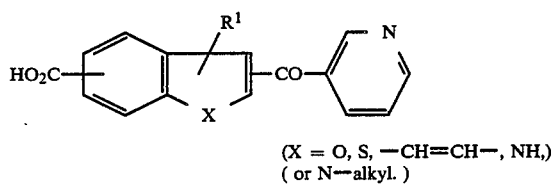

(X = O, S, —CH=CH—, NH,)
( or N—alkyl. )

(x) Compounds in which Z is S may be prepared from a suitable lithium derivative generated as described above, e.g.

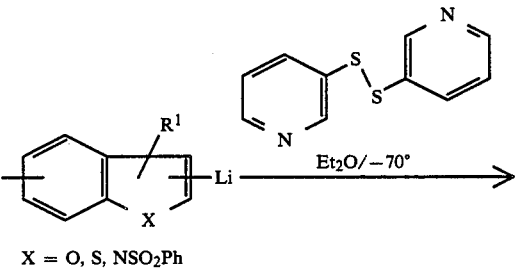

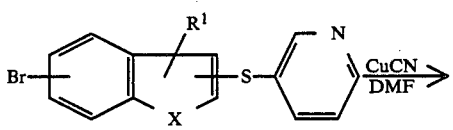

X = O, S, NSO₂Ph

-continued

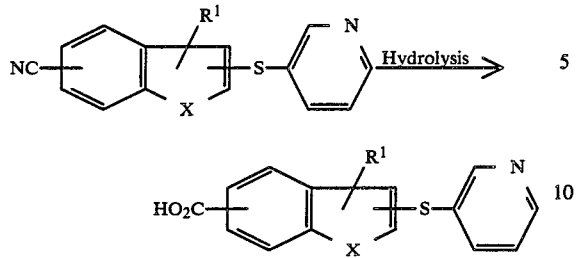

Alternatively displacement of a halogen atom (e.g. Br, I) by the anion derived from pyridine-3-thiol may be used:

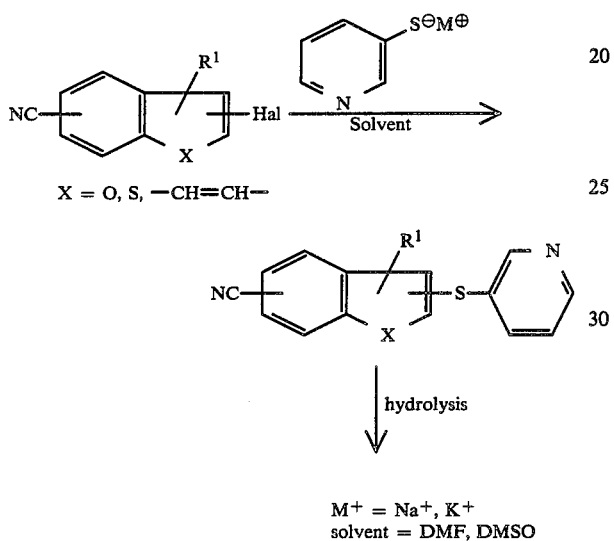

X = O, S, —CH=CH—

$M^+ = Na^+, K^+$
solvent = DMF, DMSO (xi) Compounds in which $R^1$ is Cl, Br may often be prepared by direct halogenation of analogues in which $R^1$=H, e.g.

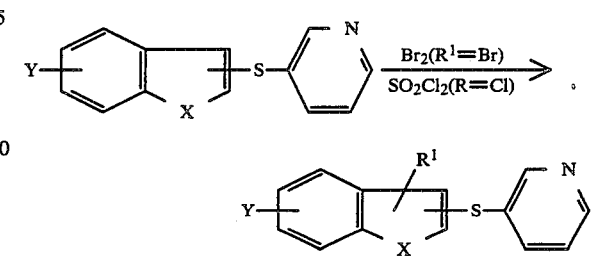

The starting materials used in the previous routes are either known compounds or are obtainable conventionally. Such preparations are illustrated in detail in the following Examples. Some illustrative routes are as follows:

Starting materials of formula

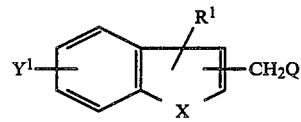

where
$Y^1$=Br,$CO_2(C_1-C_4\text{alkyl})$
X=O,S
may be prepared as shown:

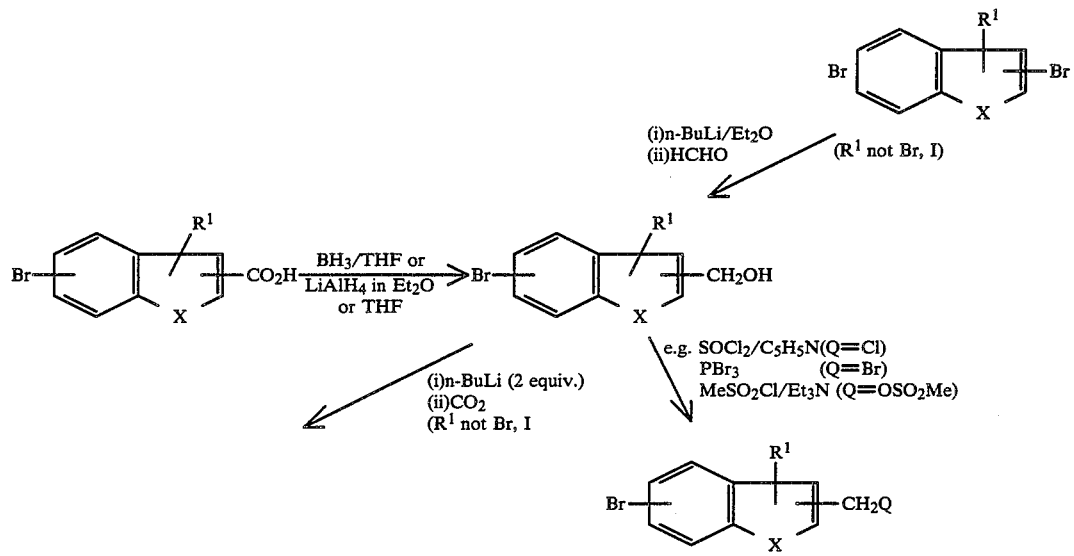

-continued

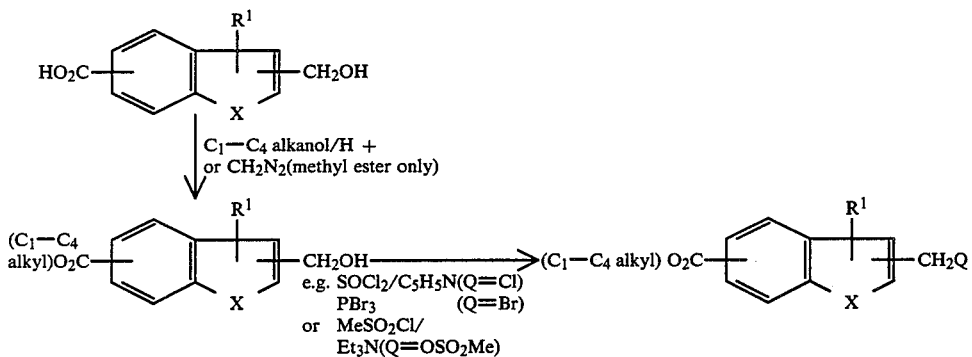

Alternatively when Q=Cl, the CH₂Cl group may be introduced by chloromethylation:

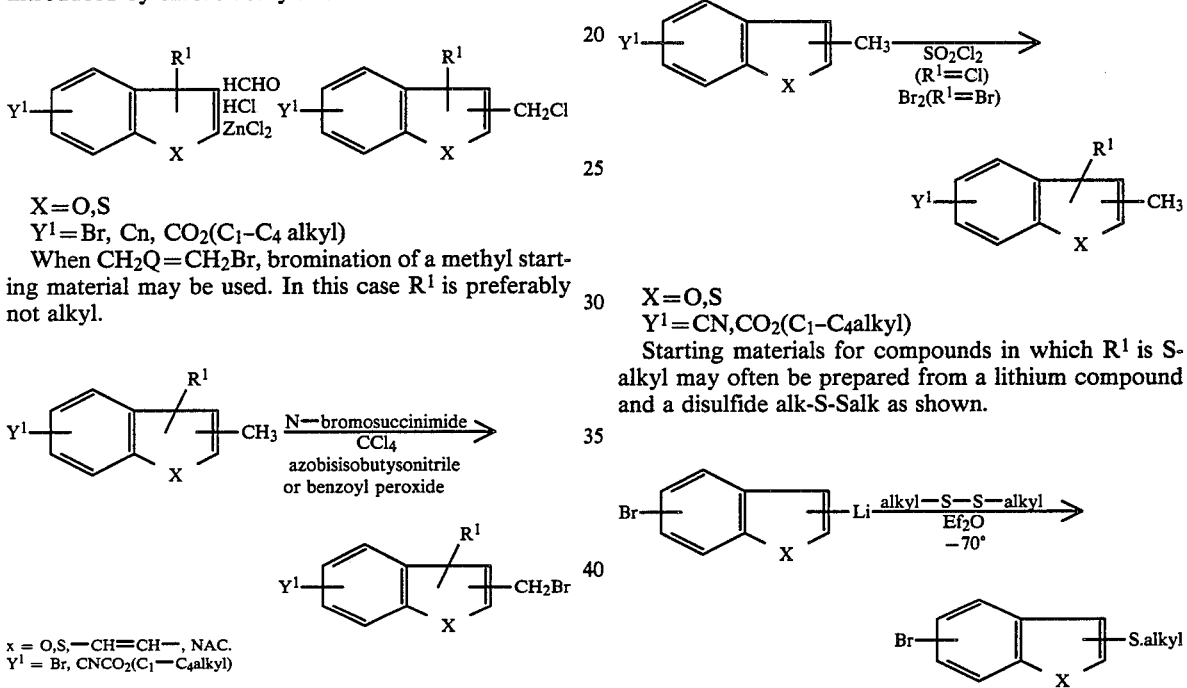

X=O,S
Y¹=Br, Cn, CO₂(C₁-C₄ alkyl)

When CH₂Q=CH₂Br, bromination of a methyl starting material may be used. In this case $R^1$ is preferably not alkyl.

x = O, S, —CH=CH—, NAC.
Y¹ = Br, CNCO₂(C₁—C₄alkyl)

Certain 3-chloro-2-hydroxymethylbenzo[b]thiophenes are available via the reaction

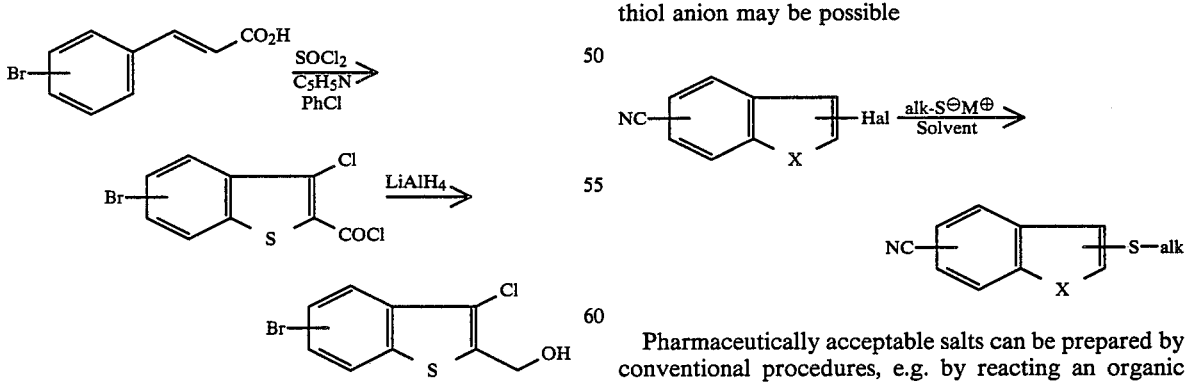

The cyclisation reaction is reported in J. Het. Chem., 8, 711, (1071) and J. Org. Chem., 41, 3399, (1976).

Intermediates in which $R^1$=halogen, especially Br or Cl, may be prepared by direct halogenation of a suitable starting material, e.g.

X=O,S
Y¹=CN,CO₂(C₁-C₄alkyl)

Starting materials for compounds in which $R^1$ is S-alkyl may often be prepared from a lithium compound and a disulfide alk-S-Salk as shown.

(X=O, S, NSO₂Ph)

Alternatively, displacement of a halogen (Br, I) by a thiol anion may be possible Pharmaceutically acceptable salts can be prepared by conventional procedures, e.g. by reacting an organic solution of the compound with an organic solution of a suitable acid to obtain an acid addition salt either by precipitation, or by evaporation of the solution. In the case of ester starting materials, often the acid used will cause hydrolysis to the free acid in addition to salt formation.

The starting materials used in the previous routes are either known compounds or can be prepared by procedures analogous to those of the prior art.

The compounds of formula (I) and their pharmaceutically acceptable salts have been found to selectively inhibit the action of the thromboxane synthetase enzyme without significantly affecting the action of the prostacyclin synthetase or cyclooxygenase enzymes. Thus the compounds are of value in the treatment of a variety of clinical conditions which are characterized by an imbalance of prostacyclin/thromboxane $A_2$. For the reasons given below these conditions include thrombosis, ischaemic heart disease, stroke, transient ischaemic attack, migraine, peripheral vascular disease, the vascular complications of diabetes and endotoxin shock.

Research work has established that in most tissues the major product of the arachidonic acid metabolism is either of two unstable substances, thromboxane $A_2$ (Tx$A_2$) or prostacyclin (PG$I_2$). (Proc. Nat. Acad. Sci. U.S.A., 1975, 72, 2994, Nature, 1976, 263, 663, Prostaglandins, 1976, 12, 897). In most cases the prostaglandins PG$E_2$, PF$G_{2\alpha}$ and PG$D_2$ are comparatively minor by-products in this biosynthetic pathway. The discovery of thromboxane $A_2$ and prostacyclin has significantly increased our understanding of vascular homeostasis. Prostacyclin for instance is a powerful vasodilator and inhibitor of platelet aggregation, and in this last respect is the most potent endogenous substance so far discovered. The prostacyclin synthetase enzyme is located in the endothelial layer of the vasculature, and may be fed by endoperoxides released by blood platelets coming into contact with the vessel wall. The prostacyclin thus produced is important for prevention of platelet deposition on vessel walls. (Prostaglandins, 1976, 12, 685, Science, 1976, 17, Nature, 1978, 273, 765).

Thromboxane $A_2$ is synthesized by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18, Prostaglandins, 1878, 13, 3). Alteration of the prostacyclin/thromboxane balance in favour of the latter substance could result in platelet aggregation, vasospasm (Lancet, 1977, 479, Science, 1976, 1135, Amer. J. Cardiology, 1978, 41, 787) and an increased susceptibility to athero-thrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thhromboxane $A_2$ was injected directly into the animal's heart (Biochem. aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a PG$I_2$/Tx$A_2$ imbalance is considered to be a contributory factor is that of migraine.

The migraine headache is associated with changes in intra and extracerebral blood flow, in particular a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250, J. Headache, 1977, 17, 101). Furthermore, it has now been postulated that not only is an abnormality of platelet function a major factor in the pathogenesis of migraine attacks but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism, 1979, 28, 394, Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of Tx$B_2$ and malondialdehyde (Symposium "Diabetes and Thrombosis—Implications for Therapy", Leeds U.K., April 1979). Also it has been shown that in rats with experimental diabetes vascular prostacyclin production is impaired and Tx$A_2$ synthesis from the platelets is elevated (IV Internation Prostaglandin Conference, Washington, D.C., May 1979). Thus the imbalance between prostacyclin and Tx$A_2$ is considered to be responsible for the microvascular complications of diabetes. A Tx$A_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the PG$G_2$/$H_2$ endoperoxides and by so doing to reduce both the prostacyclin and thromboxane $A_2$ levels. Aspirin and aspirin-like drugs have been evaluated clinically for prevention of stroke and heart attack (New England and J. Med. 1978, 299, 53, B.M.J., 1978, 1188, Stroke, 1977, 8, 301).

Although some encouraging results have been obtained with these drugs, a compound which specifically inhibits thromboxane $A_2$ formation leaving the biosynthesis of prostacyclin unimpaired would be more valuable in these clinical conditions (Lancet (ii), 1978, 780).

Shock caused by bacterial endotoxins is associated with thrombocytopaenia, disseminated intravascular coagulation, lysosomal labilisation and pulmonary and mesenteric vasoconstriction. In addition plasma thromboxane levels have been shown to rise markedly. Administration of imidazole Tx$A_2$ synthetase inhibitors to experimental animals prior to endotoxin resulted in a decrease in symptoms of shock and a markedly increased survival rate (Prostaglandins and Medicine, 4, 215, (1980) Circulatin Res., 46, 854 (1980)).

The effect of the compounds of the formula (I) on the thromboxane synthetase enzyme, and the prostacyclin synthetase and cyclooxygenase enzymes has been measured by the following in vitro enzyme assays:

1. Cyclo-oxygenase

Ram seminal vesicle microsomes (Biochemistry, 1971, 10, 2372) are incubated with arachidonic acid (100 μM:1 min.:22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45, 451) which is superfusing a spirally-cut rabbit aorta strip (Nature, 1969, 223, 29).

The ability of a compound to inhibit the enzyme is measured by comparing the increase in isometric tension produced by $PGH_2$ in the absence of the test compound, and following pre-incubation of the enzyme with the test compound for 5 minutes (Agents and Actions, 1981, 11, 274).

2. Prostacyclin ($PCI_2$) Synthetase

Pig aorta microsomes (Nature, 1976, 263, 663) are incubated (30 sec.; 22° C.) with $PGH_2$ produced as in 1 and the reaction terminated with 5 volumes of ethanol. $PGI_2$ production is assessed by measuring its stable breakdown product, 6-keto $PGH_{1\alpha}$, using a specific radioimmunoassay. $PGI_2$ production can be completely inhibited by pre-incubation of the enzyme with the selective $PGI_2$ synthetase inhibitor, 15-hydroperoxyarachidonic acid (Prostaglandins, 1976, 12, 715). The test compound is pre-incubated with the enzyme for 5 minutes, and its ability to prevent the production of $PGI_2$ (6-keto $PGF_{1\alpha}$) is measured.

3. Thromboxane $A_2$ ($TxA_2$) Synthetase

Indomethacin pretreated human platelet microsomes (Science 1976, 193, 163) are incubated (2 min.;0° C.) with $PGH_2$ (produced as in 1) and the reaction terminated with 5 volumes of ethanol. $TxA_2$ production is assessed by measuring its stable metabolite $TxB_2$, using a specific radioimmunoassay.

The test compound is pre-incubated with enzyme for 5 minutes, and its ability to inhibit the thromboxane syntehtase enzyme is measured as reduction of the $TxA_2$ ($TxB_2$) production.

Compounds of the formula (I) tested in this way have been shown to be capable of selectively inhibiting the thromboxane synthetase enzyme.

In addition to the above an in vitro assay for measuring the inhibition of human blood platelet aggregation has been described and this may be predictive of anti-thrombotic efficacy clinically (Lancet (ii), 1974, 1223, J. Exp. Med., 1967, 126, 171). Both clinically effective agents aspirin and sulphinpyrazone show inhibitory activity in vitro against a variety of aggregating agents in this test.

A number of in vivo tests in animals have also been described for evaluating potential anti-thrombotic drugs.

The method of Patrono et al is adapted to study the generation of $TxB_2$ is whole blood samples removed from animals prior to and following drug treatment. Briefly, blood samples are taken into glass tubes and allowed to clot at 37° C. Serum is separated by centrifugation and the samples stored at −40° C. until assayed for $TxB_2$, when appropriate dilutions of ethanol deproteinised samples are analysed by RIA. This technique is used in experiments with the test compounds to determine intravenous potency in anaesthetised rabbits:

Anaesthetised Rabbits

Male New Zealand white rabbits (2.6–5.6 kg) are anaesthetised with sodium pentobarbitone (30 mg/kg i.v.) followed by urethane (500 mg/kg i.p.). After cannulation of the trachea, a carotid artery is catheterised for collection of blood samples. The catheter is kept patent by slow infusion (0.2 ml/minute) of sterile saline. Control carotid arterial blood samples are taken 30 and 5 minutes prior to administration of the test compound or vehicle (0.9% w/v NaCl, 0.2 ml/kg) via a marginal ear vein. Three groups of rabbits are used. The first group receive 0.03 mg/kg of the test compound followed, one hour later, by 0.1 mg/kg. Similarly, the second group receive 0.3 mg/kg, followed by 1 mg/kg. The third group receive vehicle, followed one hour later by a further vehicle injection. Carotid arterial blood samples are taken 15 and 45 minutes after all doses. At each time point, a 1 ml blood sample is taken into a glass test tube, without anticoagulant, for $TxB_2$ determination. For the latter, the blood sample is allowed to clot during a two hour incubation at 37° C. (which preliminary experiments had shown to give maximum $TxB_2$ production) and the serum obtained by centrifugation. Serum samples are then processed through the $TxB_2$ RIA after deproteinisation with ethanol and dilution with Isogel Tris buffer.

Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138.

The compounds can be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to give tablets of the desired size. Capsules are typically prepared by granulating the ingredients together and filling them into hard gelatine capsules of the appropriate size to contain the desired dosage.

The compounds can also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3–6 using an acid such as citric, lactic or hydrochloric acid. Sufficient solutes such as dextrose or saline may be added to render the solution isotonic. The resulting solution may then be sterilised and filled into sterile glass vials of an appropriate size to contain the desired volume of solution. The compounds of the invention can be administered by the infusion of a parenteral formulation as described above into a vein.

For oral administration to human patients, the daily dosage level of a compound of the formula (I) will be from 0.1 to 20 mg/kg per day for a typical adult patient (70 kg). For parenteral administration, the daily dosage level of a compound of the formula (I) will be from 0.01–0.5 mg/kg. per day, for a typical adult patient. Thus tablets or capsules contain from 5 to 150 mg of the active compound for administration orally up to 3 times a day. Dosage units for parenteral administration will contain from 0.5–35 mg of the active compound. A typical vial would be a 10 ml vial containing 5 mg of the active compound in 6–10 ml of solution.

It should of course be appreciated that in any event the physician will determine the actual dosage which will be most suitable for the individual and it will vary with the age, weight and response of the patient.

The above dosages are exemplary of the average patient; there may of course by individual cases where higher or lower dosage ranges are merited.

The preparation of the novel compounds of the formula (I) is illustrated by the following examples. All temperatures are in °C.

EXAMPLE 1

2-(1-Imidazolylmethyl)-3-methylbenzo[b]thiophene-5-carboxylic acid ethyl ester (i) 2-Chloromethyl-3-methylbenzo[b]thiophene-5-carboxylic acid ethyl ester Hydrogen chloride gas was passed for 30 minutes through a mixture of 3-methylbenzo[b]thiophene-5-carboxylic acid ethyl ester (5.50 g), anhydrous zinc chloride (1.25 g) and paraformaldehyde (1.50 g) in chloroform (50 ml). The resulting mixture was stirred for 8 hours and then the chloroform solution was decanted off from the gummy residue, washed well with water and dried ($Na_2SO_4$). Evaporation of the solvent gave crude 2-chloromethyl-3-methylbenzo[b]thiophene-5-carboxylic acid ethyl ester which was used directly in the next stage.

(ii) 2-(1-Imidazolylmethyl)-3-methylbenzo[b]thiophene-5-carboxylic acid ethyl ester

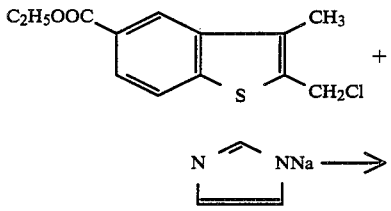

Sodium hydride (0.5 g of 50% dispersion in mineral oil) was added portionwise to a stirred solution of imidazole (0.68 g) in dry N,N-dimethylformamide (DMF) (30 ml) and the mixture was stirred at room temperature for 30 minutes. A solution of 2-chloromethyl-3-methylbenzo[b]thiophene-5-carboxylic acid ethyl ester (2.70 g) in dry N,N-dimethylformamide (5 ml) was added, the mixture was stirred for 2 hours and then evaporated. The residue was dissolved in ethyl acetate and the solution was washed well with water and dried ($Na_2SO_4$). Evaporation of the solvent gave an oil which was chromatographed on silica gel. Elution with chloroform/petrol (b.p. 40°–60° C.) (3:1) first gave some impurity followed by pure product. Evaporation of the product containing fractions gave a solid which was crystallized from ethyl acetate/petrol (b.p. 60°–80° C.) to give 2-(1-imidazolylmethyl)-3-methylbenzo[b]thiophene-5-carboxylic acid ethyl ester (1.40 g), m.p. 126°–127° C.

Analysis: Found: C,64.39; H,5.37; N,9.46. $C_{16}H_{16}N_2O_2S$, Requires: C,63.97; H,5.37; N,9.33%.

EXAMPLE 2

2-(1-Imidazolylmethyl)-3-methylbenzo[b]thiophene-5-carboxylic acid hydrochloride

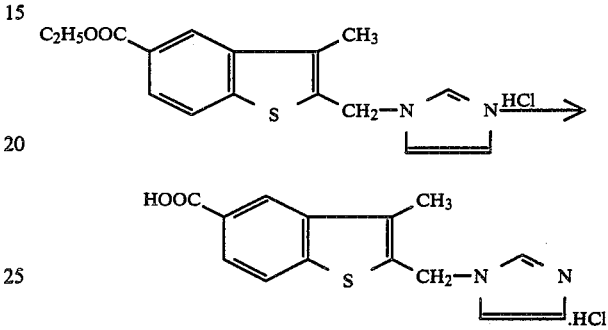

A mixture of 2-(1-imidazolylmethyl)-3-methylbenzo[b]thiophene-5-carboxylic acid ethyl ester (1.0 g) and 6N hydrochloric acid (80 ml) was heated on a steam bath for 5 hours and then cooled. The solid was filtered off, dried and crystallized from ethanol ether to give 2-(1-imidazolylmethyl)-3-methylbenzo[b]thiophene-5-carboxylic acid hydrochloride (0.72 g), m.p. 298°–299° C.

Analysis: Found: C,54.61; H,4.19; N,9.21. $C_{14}H_{12}N_2O_2S.HCl$, Requires: C,54.45; H,4.24; N,9.07%.

EXAMPLE 3

3-(3-Pyridyloxymethyl)benzo[b]thiophene-6-carboxylic acid (i) 3-Methylbenzo[b]thiophene-6-carboxylic acid A mixture of 6-bromo-3-methylbenzo[b]thiophene (16.8 g) and methyl iodide (23.8 g) was added dropwise to a stirred mixture of dry ether (150 ml) and magnesium (11.06 g) at such a rate that gentle reflux was maintained. When the addition was complete, the mixture was heated under reflux with stirring for 30 minutes, then cooled and poured onto a mixture of crushed solid carbon dioxide and ether. When all the carbon dioxide had evaporated, 2N hydrochloric acid (100 ml) was added and the mixture was shaken. The ether layer was separated and the aqueous layer was extracted with ether. The ether solutions were combined, dried ($Na_2SO_4$) and evaporated to give a solid which was crystallized from ethyl acetate to give 3-methylbenzo[b]thiophene-6-carboxylic acid (7.71 g), m.p. 230°–232° C.

Analysis: Found: C,62.49; H,4.20. $C_{10}H_8O_2S$, Requires: C,62.14; H,4.19%.

(ii) 3-Methylbenzo[b]thiophene-6-carboxylic acid methyl ester

A solution of 3-methylbenzo[b]thiophene-6-carboxylic acid (3.65 g) in methanol (100 ml) was saturated with hydrogen chloride gas and the solution was heated under reflux for 4 hours, and then evaporated. The residue was dissolved in ether and the solution was washed with water, sodium bicarbonate solution and dried ($Na_2SO_4$). Evaporation of the solvent gave 3-methylbenzo[b]thiophene-6-carboxylic acid methyl ester (3.70 g) pure enough for further reaction. A sample crystallized from petrol (b.p. 40°–60°) had m.p. 46°–47° C.

(iii) 3-Bromomethylbenzo[b]thiophene-6-carboxylic acid methyl ester

A mixture of 3-methylbenzo[b]thiophene-6-carboxylic acid methyl ester (1.03 g), N-bromosuccinimide (0.89 g), azobisisobutyronitrile (0.2 g) and carbon tetrachloride (25 ml) was heated under reflux for 2 hours and then cooled. The mixture was diluted with a few ml. of chloroform, washed with water, dried ($Na_2SO_4$) and evaporated to give a solid which was crystallized from ethyl acetate/petrol (b.p. 60°–80° C.) to give 3-bromomethylbenzo[b]thiophene-6-carboxylic acid methyl ester (0.80 g), m.p. 108°–110° C.

Analysis: Found: C,46.60; H,3.09. $C_{11}H_9BrO_2S$, Requires: C,46.33; H,3.18%.

(iv) 3-(3-Pyridyloxymethyl)benzo[b]thiophene-6-carboxylic acid methyl ester

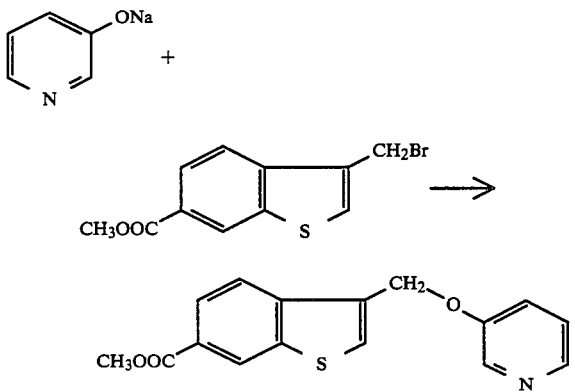

Sodium hydride (0.12 g of 50% dispersion in mineral oil) was added to a solution of 3-hydroxypyridine (0.24 g) in dry N,N-dimethylformamide (5 ml) and the mixture was stirred for 30 minutes. 3-Bromomethylbenzo[b]thiophene-6-carboxylic acid methyl ester (0.71 g) in a small volume of N,N-dimethylformamide was added and the mixture was stirred at room temperature for 2 hours and then poured into water. The mixture was extracted several times with ethyl acetate and the combined extracts were washed with water and dried ($Na_2SO_4$). Evaporation of the solvent gave a gummy solid which was chromatographed on silica gel. Elution with chloroform first gave some impurity followed by pure product. Evaporation of the product containing fractions gave 3-(3-pyridyloxymethyl)benzo[b]thiophene-6-carboxylic acid methyl ester (0.27 g) which was used directly in the next stage.

(v) 3-(3-Pyridyloxymethyl)benzo[b]thiophene-6-carboxylic acid

A mixture of the above ester (0.27 g), potassium hydroxide (0.15 g), methanol (5 ml) and water (2.5 ml) was heated under reflux for 2 hours and then evaporated. The residue was dissolved in a small volume of water and made just acidic by the addition of acetic acid. The solid was filtered off, washed with water and redissolved in potassium hydroxide solution. The solution was filtered and the filtrate was acidified with acetic acid. The solid was filtered off, washed with water and dried to give 3-(3-pyridyloxymethyl)benzo[b]thiophene-6-carboxylic acid (0.22 g), m.p. 248°–250° C.

Analysis: Found: C,63.06; H,3.87; N,4.68. $C_{15}H_{11}NO_3S$, Requires: C,63.14; H,3.89; N,4.91%.

EXAMPLE 4

2-(1-Imidazolylmethyl)benzo[b]thiophene-5-carboxylic acid methyl ester (i) 2-Methylbenzo[b]thiophene-5-carboxylic acid Conversion of 5-bromo-2-methylbenzo[b]thiophene to the Grignard reagent followed by reaction with carbon dioxide by the method of Example 3(i) gave 2-methylbenzo[b]thiophene-5-carboxylic acid, m.p. 220°–222°.

Analysis: Found: C,62.06; H,4.07. $C_{10}H_8O_2S$, Requires: C,62.14; H,4.19%.

(ii) 2-Methylbenzo[b]thiophene-5-carboxylic acid methyl ester

A solution of 2-methylbenzo[b]thiophene-5-carboxylic acid (17.4 g) in methanol (250 ml) was saturated with hydrogen chloride and then heated under reflux for 30 minutes. The solid which crystallised out on cooling was filtered off and dried to give 2-methylbenzo[b]thiophene-5-carboxylic acid methyl ester (16.7 g), m.p. 97°–98°.

Analysis: Found: C,64.39; H,4.94. $C_{11}H_{10}O_2S$, Requires: C,64.05; H,4.89%.

(iii) 2-Bromomethylbenzo[b]thiophene-5-carboxylic acid methyl ester

Treatment of 2-methylbenzo[b]thiophene-5-carboxylic acid methyl ester with N-bromosuccimimide and azobisisobutyronitrile in carbon tetrachloride by the method of Example 3(iii) gave 2-bromomethylbenzo[b]thiophene-5-carboxylic acid methyl ester, m.p. 106°–107°.

Analysis: Found: C,45.89; H,3.11. $C_{11}H_9BrO_2S$, Requires: C,46.33; H,3.18%.

(iv) 2-(1-Imidazolylmethyl)benzo[b]thiophene-5-carboxylic acid methyl ester

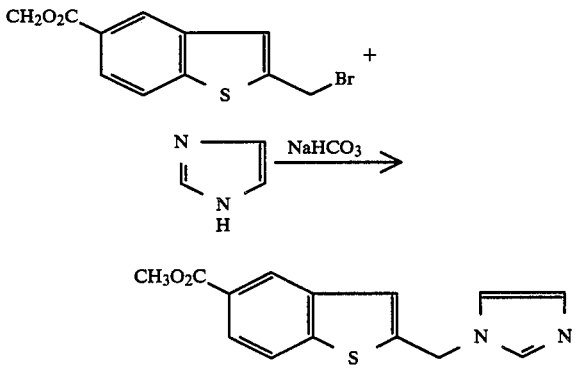

A mixture of 2-bromomethylbenzo[b]thiophene-5-carboxylic acid methyl ester (1.71 g), imidazole (4.08 g)

and sodium bicarbonate (0.55 g) in acetone (50 ml) was heated under reflux for 3 hours and then evaporated. The residue was partitioned between ethyl acetate and water. The organic layer was washed with water, dried (Na2SO4) and evaporated to give a solid which was chromatographed on silica gel. Elution with chloroform gave first a small amount of starting material followed by product. Evaporation of the product containing fractions gave a solid which was crystallised from ethyl acetate/petrol (b.p. 60°-80°) to give 2-(1-imidazolylmethyl)benzo[b]thiophene-5-carboxylic acid methyl ester (0.81 g), m.p. 127°-128°.

Analysis: Found: C,61.49; H,4.52; N,10.40. C14H12N2O2S, Requires: C,61.75; H,4.44; N,10.29%.

EXAMPLE 5

3-Chloro-2-(1-imidazolylmethyl)benzo[b]thiophene-5-carboxylic acid methyl ester (i) 3-Chloro-2-methylbenzo[b]thiophene-5-carboxylic acid methyl ester Sulphuryl chloride (3.38 g) was added dropwise to a stirred solution of 2-methylbenzo[b]thiophene-5-carboxylic acid methyl ester (5.15 g) in chloroform (50 ml). The resulting solution was heated under reflux for 2 hours, cooled, washed with water, dried (Na2SO4) and evaporated. The residue was crystallised from methanol/water to give 3-chloro-2-methylbenzo[b]thiophene-5-carboxylic acid methyl ester, 3.00 g, m.p. 85°-86°.

Analysis: Found: C,55.06; H,3.64. C11H9ClO2S, Requires: C,54.09; H, 3.77.

(ii) 2-Bromomethyl-3-chlorobenzo[b]thiophene-5-carboxylic acid methyl ester

Treatment of 3-chloro-2-methylbenzo[b]thiophene-5-carboxylic acid methyl ester with N-bromosuccimimide and azobisisobutyronitrile in carbon tetrachloride according to the method of Example 3(iii) gave 2-bromomethyl-3-chlorobenzo[b]thiophene-5-carboxylic acid methyl ester, m.p. 144°-145°.

Analysis: Found: C,41.53; H,2.56. C11H8BrClO2S, Requires: C,41.33; H,2.52%.

(iii) 3-Chloro-2-(1-imidazolylmethyl)benzo[b]thiophene-5-carboxylic acid methyl ester

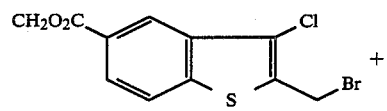

+

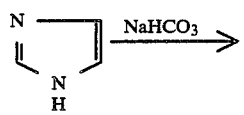

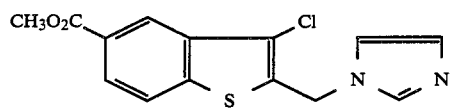

Treatment of 2-bromomethyl-3-chlorobenzo[b]thiophene-5-carboxylic acid methyl ester with imidazole and sodium bicarbonate by the method of Example 4(iv) gave 3-chloro-2-(1-imidazolylmethyl)benzo[b]thiophene-5-carboxylic acid methyl ester, m.p. 138°-139° (from ethyl acetate/petrol, b.p. 60°-80°).

Analysis: Found: C,54.74; H,3.38; N,9.39. C14H11ClN2O2S, Requires: C,54.81; H,3.61; N,9.13%.

EXAMPLE 6

3-Bromo-2-(1-imidazolylmethyl)benzo[b]thiophene-5-carboxylic acid methyl ester (i) 3-Bromo-2-methylbenzo[b]thiophene-5-carboxylic acid methyl ester Bromine (2.08 g) was added dropwise to a stirred mixture of 2-methylbenzo[b]thiophene-5-carboxylic acid methyl ester (2.40 g) and anhydrous sodium acetate (2.40 g) in chloroform (50 ml). The mixture was stirred for 2 hours at room temperature and then washed with water, sodium bicarbonate solution and dried (NaSO4). Evaporation of the chloroform gave a solid which was crystallised from methanol/water to give 3-bromo-2-methylbenzo[b]thiophene-5-carboxylic acid methyl ester (2.00 g), m.p. 84°-85°.

(ii) 3-Bromo-2-bromomethylbenzo[b]thiophene-5-carboxylic acid methyl ester

Treatment of 3-bromo-2-methylbenzo[b]thiophene-5-carboxylic acid methyl ester with N-bromosuccinimide and azobisisobutyronitrile in carbon tetrachloride by the method of Example 3(iii) gave 3-bromo-2-bromomethylbenzo[b]thiophene-5-carboxylic acid methyl ester, m.p. 173°-174° (from ethyl acetate/petrol, b.p. 60°-80°).

Analysis: Found: C,36.22; H,2.24. C11H8Br2O2S, Requires: C,36.29; H,2.21%.

(iii) 3-Bromo-2-(1-imidazolylmethyl)benzo[b]thiophene-5-carboxylic acid methyl ester

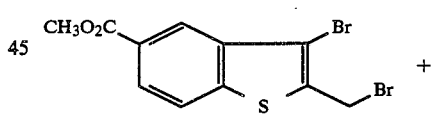

+

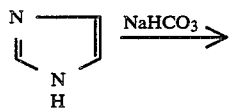

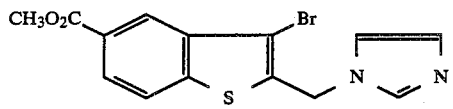

Treatment of 3-bromo-2-bromomethylbenzo[b]thiophene-5-carboxylic acid methyl ester with imidazole and sodium bicarbonate by the method of Example 4(iv) gave 3-bromo-2-(1-imidazolylmethyl)benzo[b1]thiophene-5-carboxylic acid methyl ester, m.p. 146°-147° (from ethyl acetate/petrol b.p. 60°-80°).

Analysis: Found: C,48.01; H,2.98; N,8.07. C14H11BrN2O2S, Requires: C,47.88; H,3.14; N,7.98%.

EXAMPLE 7

2-(1-Imidazolylmethyl)-3-methylthiobenzo[b]thiophene-5-carboxylic acid methyl ester (i) 5-Bromo-3-methylthiobenzo[b]thiophene A solution of n-butyl-lithium in hexane (35 ml of 1.55M solution) was added dropwise to a stirred solution of 3,5-dibromobenzo[b]thiophene (14.6 g) in dry ether (600 ml) at −70° C. under dry nitrogen. The mixture was stirred at −70° C. for 30 minutes and then a solution of dimethyl disulphide (4.90 g) in 10 ml of dry ether was added with stirring over 5 minutes. The resulting mixture was stirred at −70° C. for 4 hours and then allowed to warm up to room temperature. Water (50 ml) was added and the organic layer was separated, washed with water and dried ($Na_2SO_4$). Evaporation of the ether gave an oil which was chromatographed on silica gel. Elution with petrol (b.p. 40°–60°) gave a small amount of impurity followed by pure product. The product-containing fractions were evaporated and the residue was distilled to give 5-bromo-3-methylthiobenzo[b]thiophene (10.36 g), b.p. 140°–144° @ 0.6 mm, m.p. 56°–57°.

Analysis: Found: C,41.87; H,2.62. $C_9H_7BrS_2$, Requires: C,41.70; H,2.72%.

(ii) 3-Methylthiobenzo[b]thiophene-5-carboxylic acid

A solution of 5-bromo-3-methylthiobenzo[b]thiophene (2.60 g) and methyl iodide (4.80 g) in dry ether (50 ml) was added to a stirred mixture of magnesium (1.50 g) and dry ether (10 ml) at such a rate that gentle reflux was maintained. The mixture was heated under reflux for 30 minutes, then cooled and poured onto a mixture of crushed solid carbon dioxide and ether. When all the carbon dioxide had evaporated the mixture was shaken with 2N hydrochloric acid and the layers were separated. The ether layer was extracted several times with 2N sodium hydroxide solution and the combined extracts were acidified with acetic acid. The solid was filtered off, washed with water and crystallised from ethanol/water to give 3-methylthiobenzo[b]thiophene-5-carboxylic acid (1.24 g), m.p. 205°–207°.

Analysis: Found: C,53.23; H,3.53. $C_{10}H_8O_2S_2$, Requires: C,53.55; H,3.60%.

(iii) 3-Methylthiobenzo[b]thiophene-5-carboxylic acid ethyl ester

A mixture of 3-methylthiobenzo[b]thiophene-5-carboxylic acid (5.62 g) and phosphorous oxychloride (2 ml) in ethanol (200 ml) was heated under reflux for 18 hours and then evaporated. The residue was dissolved in ether and the solution was washed with sodium bicarbonate solution, and water and dried ($Na_2SO_4$). Evaporation of the solvent gave a solid which was crystallised from ethanol to give 3-methylthiobenzo[b]thiophene-5-carboxylic acid ethyl ester (5.84 g), m.p. 67°–69°.

Analysis: Found: C,57.25; H,4.76. $C_{12}H_{12}O_2S_2$, Requires: C,57.11; H,4.79%.

(iv) 2-Chloromethyl-3-methylthiobenzo[b]thiophene-5-carboxylic acid ethyl ester

Hydrogen chloride was passed for 2 hours through a stirred mixture of 3-methylthiobenzo[b]thiophene-5-carboxylic acid ethyl ester (1.0 g), paraformaldehyde (0.24 g) and anhydrous zinc chloride (0.2 g) in chloroform (30 ml) at 0° C. The resulting mixture was stirred at room temperature for 18 hours and then washed with water. The organic layer was separated, dried ($Na_2SO_4$) and evaporated to give an oil which was chromatographed on silica gel. Elution with toluene gave a solid which was crystallised from petrol (b.p. 60°–80°) to give 2-chloromethyl-3-methylthiobenzo[b]thiophene-5-carboxylic acid ethyl ester (0.42 g), m.p. 95°–96°.

Analysis: Found: C,51.95; H,4.31. $C_{13}H_{13}ClO_2S_2$, Requires: C,51.90; H,4.35%.

(v) 2-(1-Imidazolylmethyl)-3-methylthiobenzo[b]thiophene-5-carboxylic acid ethyl ester

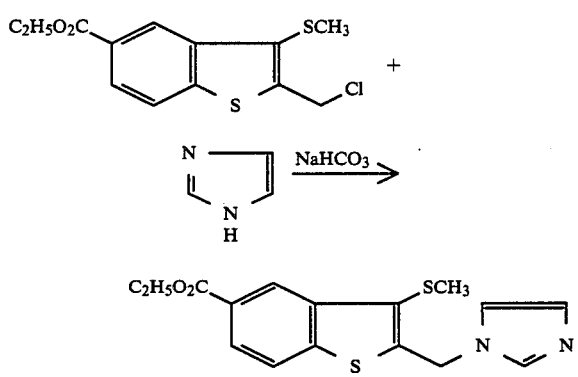

Treatment of 2-chloromethyl-3-methylthiobenzo[b]thiophene-5-carboxylic acid ethyl ester with imidazole and sodium bicarbonate by the method of Example 4(iv) gave 2-(1-imidazolylmethyl)-3-methylthiobenzo[b]thiophene-5-carboxylic acid ethyl ester, m.p. 105°–107° (from ethyl acetate petrol, b.p. 60°–80°).

Analysis: Found: C,57.73; H,4.82; N,8.55. $C_{16}H_{16}N_2O_2S_2$, Requires: C,57.80; H,4.85; N,8.43%.

EXAMPLE 8

2-(1-Imidazolylmethyl)-3-methylbenzo[b]thiophene-6-carboxylic acid (i) 6-Bromo-2-hydroxymethyl-3-methylbenzo[b]thiophene A solution of n-butyl-lithium in hexane (13.2 ml of 1.55M solution) was added dropwise to a stirred solution of 2,6-dibromo-3-methylbenzo[b]thiophene (6.60 g) in dry ether (150 ml) at 0° under dry nitrogen and the mixture was stirred at 0° for 30 minutes. Paraformaldehyde (0.71 g) was then added portionwise and the mixture was stirred at 0° for 3 hours. Water was added and the layers were separated. The ether layer was washed with water, dried ($Na_2SO_4$) and evaporated to give an oil which was chromatographed on silica gel. Elution with chloroform first gave some impurity followed by pure product. Evaporation of the product-containing fractions gave a solid which was crystallised from ethyl acetate/petrol (b.p. 60°–80°) to give 6-bromo-2-hydroxymethyl-3-methylbenzo[b]thiophene (3.20 g), m.p. 95°–96°.

Analysis: Found: C,46.97; H,3.49. $C_{10}H_9BrOS$, Requires: C,46.70; H,3.53%.

(ii) 6-Bromo-2-chloromethyl-3-methylbenzo[b]thiophene

Thionyl chloride (2.0 ml) was added dropwise to a stirred solution of 6-bromo-2-hydroxymethyl-3-methylbenzo[b]thiophene (3.60 g) and pyridine (3 drops) in chloroform (80 ml). The solution was stirred at room temperature for 1 hour, then washed with water, sodium bicarbonate solution and dried ($Na_2SO_4$). Evaporation of the solvent gave a quantitative yield of 6-bromo-2-chloromethyl-3-methylbenzo[b]thiophene. A sample crystallised from petrol (b.p. 40°–60°) had m.p. 92°–93°.

Analysis: Found: C,43.51; H,3.00. $C_{10}H_8BrClS$, Requires: C,43.58; H,2.92%.

(iii)
6-Bromo-2-(1-imidazolylmethyl)-3-methylbenzo[b]thiophene

Treatment of 6-bromo-2-chloromethyl-3-methylbenzo[b]thiophene with imidazole and sodium bicarbonate by the method of Example 4(iv) gave 6-bromo-2-(1-imidazolylmethyl)-3-methylbenzo[b]thiophene, m.p. 138°–139° (from ethyl acetate/petrol, b.p. 60°–80°).

Analysis: Found: C,50.49; H,3.57; N,9.19. $C_{13}H_{11}BrN_2S$, Requires: C,50.82; H,3.61; N,9.12%.

(iv)
2-(1-Imidazolylmethyl)-3-methylbenzo[b]thiophene-6-carbonitrile

A mixture of 6-bromo-2-(1-imidazolylmethyl)-3-methylbenzo[b]thiophene (1.01 g) and cuprous cyanide (1.80 g) in N,N-dimethylformamide (20 ml) was heated under reflux for 22 hours and then cooled and poured into water. The solid was filtered off, washed with water and then suspended in a mixture of concentrated aqueous ammonia solution (100 ml) and ethyl acetate (150 ml) and the mixture was stirred until no solid remained. The organic layer was separated, washed with water, dried ($Na_2SO_4$) and evaporated. The residue was crystallised from ethyl acetate/petrol (b.p. 60°–80°) to give 2-(1-imidazolylmethyl)-3-methylbenzo[b]thiophene-6-carbonitrile (0.58 g), m.p. 154°–155°.

Analysis: Found: C,66.04; H,4.50; N,16.61. $C_{14}H_{11}N_3S$, Requires: C,66.37; H,4.38; N,16.59%.

(v)
2-(1-Imidazolylmethyl)-3-methylbenzo[b]thiophene-6-carboxylic acid

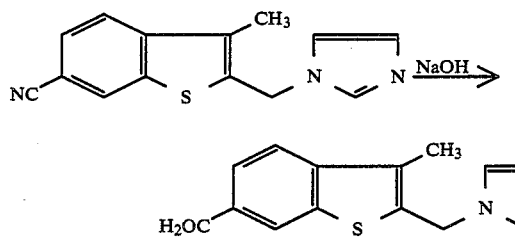

A mixture of 2-(1-imidazolylmethyl)-3-methylbenzo[b]thiophene-6-carbonitrile (0.40 g), sodium hydroxide (0.20 g), ethanol (2 ml) and water (20 ml) was heated under reflux for 24 hours. The solution was evaporated and the residue was dissolved in water and the solution was acidified with acetic acid. The solid was filtered off and purified by redissolving in dilute sodium hydroxide solution, filtering and acidifying the filtrate with acetic acid. The solid was filtered off, washed with water and dried to give 2-(1-imidazolylmethyl)-3-methylbenzo[b]thiophene-6-carboxylic acid (0.35 g), m.p. 254°–255°.

Analysis: Found: C,61.37; H,4.60; N,10.19. $C_{14}H_{12}N_2O_2S$, Requires: C,61.74; H,4.44; N,10.29%.

EXAMPLE 9

3-Methyl-2-(3-pyridylmethyl)benzo[b]thiophene-6-carboxylic acid (i) 6-Bromo-3-methylbenzo[b]thien-2-yl pyrid-3-yl ketone A solution of n-butyl-lithium in hexane (16.3 ml of 1.55M solution) was added to a stirred solution of 2,6-dibromo-3-methylbenzo[b]thiophene (7.65 g) in dry ether (150 ml) at −70° under dry nitrogen. The mixture was stirred for 30 minutes at −70° and then 3-cyanopyridine (2.60 g) in dry ether (50 ml) was added dropwise over 5 minutes. The resulting mixture was stirred at −70° for 3 hours and then at room temperature for a further 2 hours. Concentrated hydrochloric acid (40 ml) was added dropwise with stirring and the layers were separated. The ether layer was extracted with concentrated hydrochloric acid (20 ml) and the acid extracts were combined and warmed to complete hydrolysis of the intermediate ketimine salt. The solution was cooled and made alkaline with sodium hydroxide solution. The mixture was extracted several times with ethyl acetate and the combined extracts were washed with water and dried ($Na_2SO_4$). Evaporation of the solvent gave a solid which was chromatographed on silica gel. Elution with chloroform/petrol (b.p. 40°–60°) (2:1) gave a solid which was crystallised from ethyl acetate/petrol (b.p. 40°–60°) to give 6-bromo-3-methylbenzo[b]thien-2-yl pyrid-3-yl ketone (4.70 g), m.p. 110°–111°.

Analysis: Found: C,53.93; H,3.17; N,4.29. $C_{15}H_{16}BrNOS$, Requires: C,54.22; H,3.03; N,4.22%.

(ii)
6-Bromo-3-methyl-3-(3-pyridylmethyl)benzo[b]thiophene

A mixture of 6-bromo-3-methylbenzo[b]thien-2-yl pyrid-3-yl ketone (4.30 g) and hydrazine hydrate (2.60 g) in ethylene glycol (30 ml) was heated under reflux for 2 hours and then cooled. Potassium hydroxide (2.80 g) was added and the temperature was gradually raised to reflux. After heating under reflux for a further 3 hours the solution was cooled and poured into water. The mixture was extracted several times with ethyl acetate and the combined extracts were washed with water and dried ($Na_2SO_4$). Evaporation of the solvent gave a solid which was chromatographed on silica gel. Elution with chloroform/petrol (b.p. 40°–60°). (3:1) gave 6-bromo-3-methyl-2-(3-pyridylmethyl)benzo[b]thiophene (3.20 g). A sample crystallised from petrol (b.p. 40°–60°) had m.p. 69°–70°.

Analysis: Found: C, 56.65; H, 3.86; N, 4.84. $C_{15}H_{12}Br_2NS$, Requires: C, 56.61; H, 3.80; N, 4.40%.

(iii)
3-Methyl-2-(3-pyridylmethyl)benzo[b]thiophene-6-carbonitrile

Treatment of 6-bromo-3-methyl-2-(3-pyridylmethyl)benzo[b]thiophene with cuprous cyanide in N,N-dimethylformamide by the method of Example 8(iv) gave 3-methyl-2-(3-pyridylmethyl)benzo[b]thiophene-6-carbonitrile, m.p. 115°–116° (from ethyl acetate/petrol, b.p. 40°–60°).

Analysis: Found: C, 72.66; H, 4.60; N, 10.80. $C_{16}H_{12}N_2S$, Requires: C, 72.69; H, 4.58; N, 10.60%.

(iv) 3-Methyl-2-(3-pyridylmethyl)benzo[b]thiophene-6-carboxylic acid

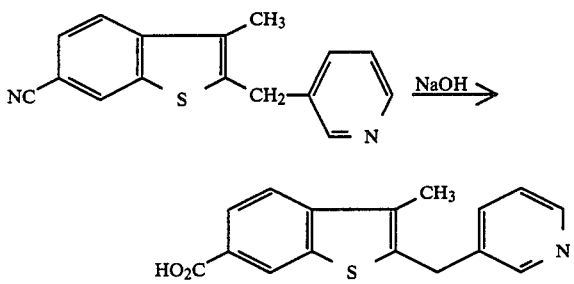

Hydrolysis of 3-methyl-2-(3-pyridylmethyl)benzo[b]thiophene-6-carbonitrile by the method of Example 8(v) gave 3-methyl-2-(3-pyridylmethyl)benzo[b]thiophene-6-carboxylic acid, m.p. 248°–249°.

Analysis: Found: C, 68.12; H, 4.65; N, 4.96. $C_{16}H_{13}NO_2S$, Requires: C, 67.82; H, 4.62; N, 4.94%.

EXAMPLE 10

3-Methyl-2-(3-pyridylmethyl)benzo[b]thiophene-5-carboxylic acid (i) 2,5-Dibromo-3-methylbenzo[b]thiophene A solution of bromine (3.20 g) in chloroform (10 ml) was added dropwise to a stirred solution of 5-bromo-3-methylbenzo[b]thiophene (4.54 g) in chloroform (40 ml) and the solution was stirred at room temperature for 1.5 hours. It was then washed with dilute sodium hydroxide solution, water and dried ($Na_2SO_4$). Evaporation of the solvent gave a solid which was crystallised from petrol (b.p. 80°–100°) to give 2,5-dibromo-3-methylbenzo[b]thiophene (5.45 g), m.p. 118°–122°.

Analysis: Found: C, 35.53; H, 1.91. $C_9H_6Br_2S$, Requires: C, 35.32; H, 1.98%.

(ii) 5-Bromo-3-methylbenzo[b]thien-2-yl pyrid-3-yl ketone

Successive treatment of 2,5-dibromo-3-methylbenzo[b]thiophene with n-butyl-lithium and 3-cyanopyridine by the method of Example 9(i) gave 5-bromo-3-methylbenzo[b]thien-2-yl pyrid-3-yl ketone, characterised as the hydrochloride salt, m.p. 193°–195°.

Analysis: Found: C, 48.50; H, 3.00; N, 3.94. $C_{15}H_{10}BrNOS.HCl$, Requires: C, 48.86; H, 3.01, N, 3.80%.

(iii) 5-Bromo-3-methyl-2-(3-pyridylmethyl(benzo[b]thiophene

Successive treatment of 5-bromo-3-methylbenzo[b]thien-2-yl pyrid-3-yl ketone with hydrazine hydrate and potassium hydroxide in ethylene glycol by the method of Example 9(ii) gave 5-bromo-3-methyl-2-(3-pyridylmethyl)benzo[b]thiophene, characterised as the hydrochloride salt, m.p. 201°–203°.

Analysis: Found: C, 50.89; H, 3.46; N, 4.23. $C_{15}H_{12}BrNS.HCl$, Requires: C, 50.79; H, 3.69; N, 3.95%.

(iv) 3-Methyl-2-(3-pyridylmethyl)benzo[b]thiophene-5-carbonitrile

Treatment of 5-bromo-3-methyl-2-(3-pyridylmethyl)benzo[b]thiophene with cuprous cyanide in N,N-dimethylformamide by the method of Example 8(iv) gave 3-methyl-2-(3-pyridylmethyl)benzo[b]thiophene-5-carbonitrile, m.p. 149°–152° (from ethyl acetate/petrol, b.p. 60°–80°).

Analysis: Found: C, 72.56; H, 4.52; N, 10.61. $C_{16}H_{12}N_2S$, Requires: C, 72.69; H, 4.58; N, 10.60%.

(v) 3-Methyl-2-(3-pyridylmethyl)benzo[b]thiophene-5-carboxylic acid

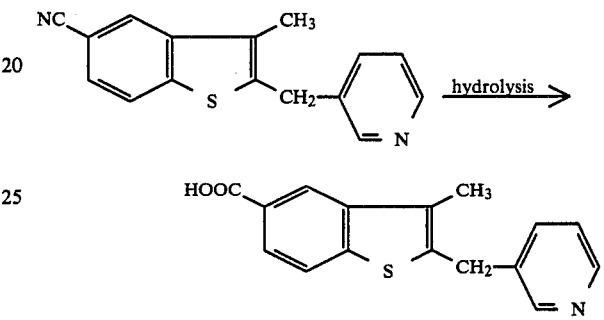

Hydrolysis of 3-methyl-2-(3-pyridylmethyl)benzo[b]thiophene-5-carbonitrile by the method of Example 8(v) gave 3-methyl-2-(3-pyridylmethyl)benzo[b]thiophene-5-carboxylic acid, m.p. 230°–232°.

Analysis: Found: C, 67.69; H, 4.62; N, 4.90. $C_{16}H_{13}NO_2S$, Requires: C, 67.82; H, 4.62; N, 4.94%.

EXAMPLE 11

2-(3-Pyridylmethyl)benzo[b]thiophene-5-carboxylic acid (i) 5-Bromobenzo[b]thien-2-yl pyrid-3-yl ketone A solution of n-butyl-lithium in hexane (25.8 ml of 1.55M solution) was added dropwise to a stirred solution of 3-bromobenzo[b]thiophene (8.50 g) in dry ether (120 ml) at −20° under nitrogen and the mixture was stirred at 0° for 30 minutes. Treatment of the resulting lithium compound with 3-cyanopyridine (4.50 g) at −70° as described for Example 9(i) gave 5-bromobenzo[b]thien-2-yl pyrid-3-yl ketone (4.73 g), m.p. 147°–148° (from ethyl acetate/petrol, b.p. 60°–80°).

Analysis: Found: C, 53.07; H, 2.55; N, 4.49. $C_{14}H_8BrNOS$, Requires: C, 52.84; H, 2.53; N, 4.40%.

(ii) 5-Bromo-2-(3-pyridylmethyl)benzo[b]thiophene

Successive treatment of 5-bromobenzo[b]thien-2-yl pyrid-3-yl ketone with hydrazine hydrate and potassium hydroxide in ethylene glycol by the method of Example 9(ii) gave 5-bromo-2-(3-pyridylmethyl)benzo[b]thiophene, m.p. 102°–103° (from ethyl acetate/petrol, b.p. 60°–80°).

Analysis: Found: C, 55.61; H, 3.25; N, 4.75. $C_{14}H_{10}BrNS$, Requires: C, 55.27; H, 3.31; N, 4.60%.

(iii) 2-(3-Pyridylmethyl)benzo[b]thiophene-5-carbonitrile

Treatment of 5-bromo-2-(3-pyridylmethyl)benzo[b]thiophene with cuprous cyanide in N,N-dimethylformamide by the method of Example 8(iv) gave 2-(3-pyridyl-methyl)benzo[b]thiophene-5-carbonitrile, m.p. 59°–62°.

Analysis: Found: C, 71.54; H, 3.99; N, 10.65. $C_{15}H_{10}N_2S$, Requires: C, 71.97; H, 4.03; N, 11.19%.

(iv)
2-(3-Pyridylmethyl)benzo[b]thiophene-5-carboxylic acid

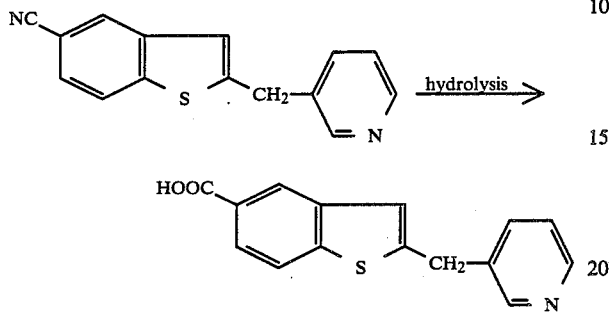

Hydrolysis of 2-(3-pyridylmethyl)benzo[b]thiophene-5-carbonitrile by the method of Example 8(v) gave 2-(3-pyridylmethyl)benzo[b]thiophene-5-carboxylic acid, m.p. 246°–249° (from ethanol).

Analysis: Found: C, 66.84; H, 4.24; N, 5.13. $C_{14}H_{10}NO_2S$, Requires: C, 66.89; H, 4.12; N, 5.20%.

EXAMPLE 12

3-Methyl-2-(3-pyridylthio)benzo[b]thiophene-5-carboxylic acid (i)
5-Bromo-3-methyl-2-(3-pyridylthio)benzo[b]thiophene A solution of n-butyl-lithium in hexane (10.3 ml of 1.55M solution) was added dropwise to a stirred solution of 2,5-dibromo-3-methylbenzo[b]thiophene (the product of Example 10(i)) (4.90 g) in dry ether (175 ml) at 0° under nitrogen. The mixture was stirred at at 0° for 30 minutes and then cooled to −70°. A solution of 3,3'-dipyridyl disulphide (3.50 g) in dry ether (25 ml) was added over 3 minutes with stirring. The cooling bath was removed and the mixture was allowed to warm up to room temperature with stirring. An excess of water was then added and the layers were separated. The aqueous layer was extracted several times with ether and the combined organic layer and extracts were washed with water and dried ($Na_2SO_4$). Evaporation of the solvent gave an oil which was chromatographed on silica gel. Elution with toluene first gave more impurity followed by product. Evaporation of the product containing fractions gave 5-bromo-3-methyl-2-(3-pyridylthio)benzo[b]thiophene (1.80 g) pure enough for further reaction. A sample crystallised from petrol (b.p. 40°–60°) had m.p. 86°–87°.

Analysis: Found: C, 49.96; H, 2.92; N, 4.03. $C_{14}H_{10}BrNS_2$, Requires: C, 50.01; H, 3.00; N, 4.17%.

(ii)
3-Methyl-2-(3-pyridylthio)benzo[b]thiophene-5-carbonitrile

Treatment of 5-bromo-3-methyl-2-(3-pyridylthio)benzo[b]thiophene with cuprous cyanide in N,N-dimethylformamide by the method of Example 8(iv) gave 3-methyl-2-(3-pyridylthio)benzo[b]thiophene-5-carbonitrile, m.p. 125°–128° (from MeOH/$H_2O$).

Analysis: Found: C, 63.72; H, 3.71; N, 9.64. $C_{15}H_{10}N_2S_2$, Requires: C, 63.80; H, 3.57; N, 9.92%.

(iii)
3-Methyl-2-(3-pyridylthio)benzo[b]thiophene-5-carboxylic acid

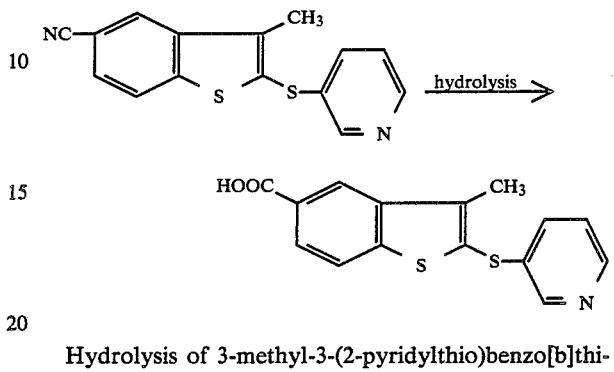

Hydrolysis of 3-methyl-3-(2-pyridylthio)benzo[b]thiophene-5-carbonitrile by the method of Example 8(v) gave 3-methyl-2-(3-pyridylthio)benzo[b]thiophene-5-carboxylic acid, m.p. 220°–222°.

Analysis: Found: C, 59.94; H, 3.83; N, 4.80. $C_{15}H_{11}NO_2S_2$, Requires: C, 59.78; H, 3.68; N, 4.65%.

EXAMPLE 13

3-Methyl-2-(3-pyridylmethyl)benzo[b]thiophene-5-carboxamide

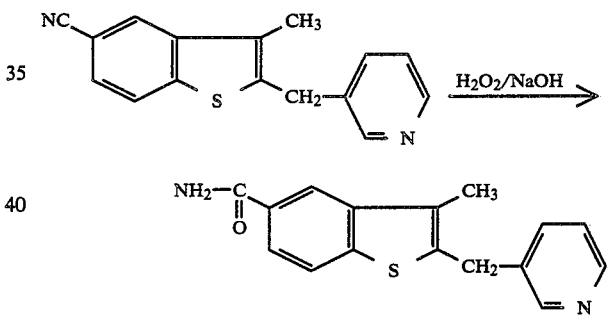

Hydrogen peroxide (1.6 ml of 30% w/v solution) was added to a stirred solution of 3-methyl-2-(3-pyridylmethyl)benzo[b]thiophene-5-carbonitrile (the product of Example 12(ii)) (0.30 g) in ethanol (3.5 ml) followed by 6N sodium hydroxide solution (1.6 ml). The resulting mixture was heated at 50°–55° C. with stirring for 2 hours and then cooled and poured into water. The solid was filtered off, washed with water and crystallised from ethanol/water to give 3-methyl-2-(3-pyridylmethyl)benzo[b]thiophene-5-carboxamide (0.21 g), m.p. 194°–195°.

Analysis: Found: C, 67.91; H, 5.04; N, 9.66. $C_{16}H_{14}N_2OS$, Requires: C, 68.06; H, 5.00; N, 9.92%.

EXAMPLE 14

3-Methyl-2-(3-pyridylmethyl)benzofuran-5-carboxylic acid (i) 5-Bromo-3-methylbenzofuran-2-yl pyrid-3-yl ketone hydrochloride A mixture of 3-bromoacetylpyridine hydrobromide (1.50 g) and finely ground anhydrous potassium carbonate (2.20 g) was added to a stirred solution of 5-bromo- 2-hydroxyacetophenone (1.10 g) in dry acetone (50 ml) at 5°. The mixture was stirred at 5° for 30 minutes and then at room temperature for 24 hours. It was then filtered and the solid was washed with acetone. The combined filtrate and washings were evaporated and the residue was extracted several times with ether. The combined ether extracts were filtered and an excess of ethereal hydrogen chloride was added. The solid was filtered off, washed with ether and dried to give 5-bromo-3-methylbenzofuran-2-yl pyrid-3-yl ketone hydrochloride (1.07 g), m.p. 193°–197°.

Analysis: Found: C, 50.99; H, 3.09; N, 4.22. $C_{15}H_{10}BrNO_2.HCl$, Requires: C, 51.09; H, 3.15; N, 3.97%.

(ii) 5-Bromo-3-methyl-2-(3-pyridylmethyl)benzofuran

A mixture of 5-bromo-3-methylbenzofuran-2-yl pyrid-3-yl ketone free base (2.67 g) and hydrazine hydrate (1.80 g) in ethylene glycol (30 ml) was heated at 120° C. for 2.5 hours. The mixture was cooled, potassium hydroxide (1.80 g) was added and the temperature was raised to 120° again and maintained at this temperature for 1 hour. Dilution with water and ether extraction gave an oil which was chromatographed on silica gel. Elution with chloroform gave a solid which was crystallised from petrol (b.p. 80°–100°) to give 5-bromo-3-methyl-2-(3-pyridylmethyl)benzofuran (2.00 g), m.p. 57°–58°.

Analysis: Found: C, 59.81; H, 4.01; N, 4.74. $C_{15}H_{12}BrNO$, Requires: C, 59.62; H, 4.00; N, 4.64%.

(iii) 3-Methyl-2-(3-pyridylmethyl)benzofuran-5-carbonitrile

Treatment of 5-bromo-3-methyl-2-(3-pyridylmethyl)benzofuran with cuprous cyanide according to the method of Example 8(iv) gave 3-methyl-2-(3-pyridylmethyl)benzofuran-5-carbonitrile which was used directly in the next stage.

Accurate mass measurement: Found: 248.0960, Requires: 248.09489.

(iv) 3-Methyl-2-(3-Pyridylmethyl)benzofuran-5-carboxylic acid

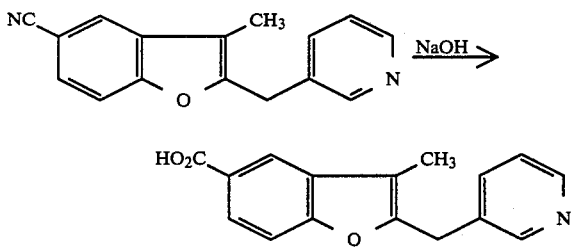

Hydrolysis of 3-methyl-2-(3-pyridylmethyl)benzofuran-5-carbonitrile by the method of Example 8(v) gave 3-methyl-2-(3-pyridylmethyl)benzofuran-5-carboxylic acid, m.p. 219°–221°.

Analysis: Found: C, 71.61; H, 4.65; N, 5.14. $C_{16}H_{13}NO_3$, Requires: C, 71.90; H, 4.90; N, 5.24%.

EXAMPLE 15

3-Methyl-2-(1-imidazolylmethyl)benzofuran-5-carboxylic acid methyl ester (i) 2-Hydroxymethyl-3-methylbenzofuran-5-carboxylic acid A solution of 5-bromo-2-hydroxymethyl-3-methylbenzofuran (Annalen, 1112, 1973) (1.93 g) in dry ether (50 ml) was added dropwise to a stirred solution of n-butyl-lithium (12.90 ml of 1.55M solution in hexane) in dry ether (50 ml) at 0° C. under an atmosphere of dry nitrogen. The mixture was stirred at 0° for 2 hours and then poured onto a mixture of crushed solid carbon dioxide and ether. When all the carbon dioxide had evaporated the mixture was shaken with water. The aqueous layer was separated, washed with ether and acidified with concentrated hydrochloric acid. The solid was filtered off, washed with water, dried and crystallised from isopropanol/petrol (b.p. 80°–100°) to give 2-hydroxymethyl-3-methylbenzofuran-5-carboxylic acid (0.50 g), m.p. 220°–222°.

Analysis: Found: C, 64.31; H, 4.96. $C_{11}H_{10}O_4$, Requires: C, 64.08; H, 4.89%.

(ii) 2-Hydroxymethyl-3-methylbenzofuran-5-carboxylic acid methyl ester

A solution of 2-hydroxymethyl-3-methylbenzofuran-5-carboxylic acid (0.69 g) in methanol (250 ml) was treated with an excess of an ethereal solution of diazomethane. The solution was allowed to stand for 1½ hours at 0° and then the excess of diazomethane was decomposed by dropwise addition of acetic acid until no further effervescence was apparent. The solution was evaporated and the residue was dissolved in ether. The solution was washed with sodium bicarbonate, dried ($Na_2SO_4$) and evaporated to give a quantitative yield of 2-hydroxymethyl-3-methylbenzofuran-5-carboxylic acid methyl ester, m.p. 96°–98° (from ethyl acetate/petrol).

Analysis: Found: C, 65.28; H, 5.49. $C_{12}H_{12}O_4$, Requires: C, 65.44; H, 5.49%.

(iii) 2-Chloromethyl-3-methylbenzofuran-5-carboxylic acid methyl ester

Thionyl chloride (0.25 ml) was added dropwise to a stirred solution of 2-hydroxymethyl-3-methylbenzofuran-5-carboxylic acid methyl ester (0.20 g) and pyridine (2 drops) in chloroform (5 ml). The solution was stirred at room temperature for 30 minutes and then washed successively with water, sodium bicarbonate solution and dried ($Na_2SO_4$). Evaporation of the solvent gave crude 2-chloromethyl-3-methylbenzofuran-5-carboxylic acid methyl ester (0.18 g), m.p. 114°–115° which was used directly in the next stage.

(iv) 2-(1-Imidazolylmethyl)-3-methylbenzofuran-5-carboxylic acid methyl ester

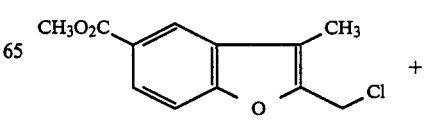

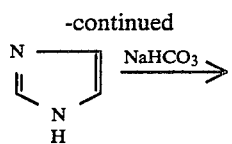

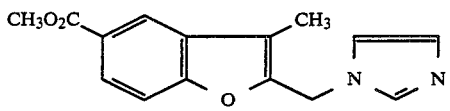

Treatment of 2-chloromethyl-3-methylbenzofuran-5-carboxylic acid methyl ester with imidazole and sodium bicarbonate by the method of Example 4(iv) gave 2-(1-imidazolylmethyl)-3-methylbenzofuran-5-carboxylic acid methyl ester, m.p. 135°-136°. The product was not characterised further.

EXAMPLE 16

3-Chloro-2-(1-imidazolylmethyl)benzofuran-5-carboxylic acid (i) 3-Chloro-2-methylbenzofuran-5-carbonitrile A solution of 2-methylbenzofuran-5-carbonitrile (J. Het. Chem., 4, 441, 1967) (1.52 g) and sulphuryl chloride (1.49 g) in chloroform (25 ml) was heated under reflux for 9 hours and then cooled. The solution was washed successively with water, dilute sodium hydroxide solution, water and then dried ($Na_2SO_4$). Evaporation of the solvent gave a solid which was crystallised twice from methanol to give 3-chloro-2-methylbenzofuran-5-carbonitrile (0.45 g), m.p. 131.5°-133.5°.

Analysis: Found: C, 62.82; H, 3.17; N, 7.34. $C_{10}H_6ClNO$, Requires: C, 62.68; H, 3.16; N, 7.31%.

(ii) 2-Bromomethyl-3-chlorobenzofuran-5-carbonitrile

Treatment of 3-chloro-2-methylbenzofuran-5-carbonitrile with N-bromosuccinimide and azobisisobutyronitrile in carbon tetrachloride by the method of Example 3(iii) gave 2-bromomethyl-3-chlorobenzofuran-5-carbonitrile, m.p. 124°-127° (from ethyl acetate/petrol, b.p. 80°-100°).

Analysis: Found: C, 44.71; H, 1.94; N, 5.49. $C_{10}H_5BrClNO$, Requires: C, 44.40; H, 1.86; N, 5.18%.

(iii) 3-Chloro-2-(1-imidazolylmethyl)benzofuran-5-carbonitrile

Treatment of 2-bromomethyl-3-chlorobenzofuran-5-carbonitrile with imidazole and sodium bicarbonate by the method of Example 4(iv) gave 3-chloro-2-(1-imidazolylmethyl)benzofuran-5-carbonitrile, m.p. 231°-233° (from ethyl acetate/petrol, b.p. 60°-80°).

Analysis: Found: C, 60.65; H, 3.11; N, 16.42. $C_{13}H_8ClN_3O$, Requires: C, 60.59; H, 3.13; N, 16.31%.

(iv) 3-Chloro-2-(1-imidazolylmethyl)benzofuran-5-carboxylic acid

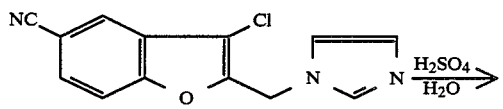

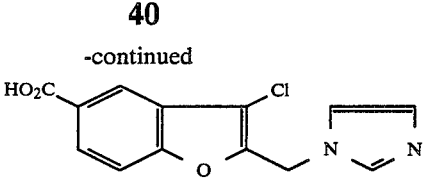

A solution of 3-chloro-2-(1-imidazolylmethyl)benzofuran-5-carbonitrile (0.35 g) in concentrated sulphuric acid (5 ml) and water (5 ml) was heated under reflux for 1 hour and then cooled. The solution was diluted with 5 ml of water and made just alkaline by the addition of 5N sodium hydroxide solution. The solution was filtered and made acidic by the addition of acetic acid. The solid which crystallised out on standing was filtered off, washed with water and dried to give 3-chloro-2-(1-imidazolylmethyl)benzofuran-5-carboxylic acid (0.20 g), m.p. 248°-250°.

Analysis: Found: C, 56.27; H, 3.35; N, 10.24. $C_{13}H_9ClN_2O_3$, Requires: C, 56.43; H, 3.28; N, 10.13%.

EXAMPLE 17

3-Bromo-2-(1-imidazolylmethyl)benzofuran-5-carboxylic acid (i) 3-Bromo-2-methylbenzofuran-5-carbonitrile Bromine (3.20 g), was added dropwise to a stirred mixture of 2-methylbenzofuran-5-carbonitrile (3.04 g) and anhydrous sodium acetate (2.0 g) in acetic acid (30 ml) and the mixture was stirred at room temperature for 1 hour and then poured into water (ca 200 ml). The mixture was extracted several times with chloroform and the combined extracts were washed successively with water, dilute sodium hydroxide solution, water and dried ($Na_2SO_4$). Evaporation of the solvent gave a gummy solid which was triturated with a few ml of methanol and filtered. The solid was washed with a little methanol and dried to give 3-bromo-3-methylbenzofuran-5-carbonitrile (3.44 g), m.p. 163°-165°, raised to 164°-166° on crystallisation from isopropanol/petrol (b.p. 60°-80°).

Analysis: Found: C,50.98; H,2.62; N,6.09. $C_{10}H_6BrNO$, Requires: C,50.87; H,2.56; N,5.93%.

(ii) 3-Bromo-2-bromomethylbenzofuran-5-carbonitrile

Treatment of 3-bromo-2-methylbenzofuran-5-carbonitrile with N-bromosuccinimide and azobisisobutyronitrile in carbon tetrachloride by the method of Example 3(iii) gave 3-bromo-2-bromomethylbenzofuran-5-carbonitrile, m.p. 129°-131° (from ethyl acetate/petrol, b.p. 80°-100°).

Analysis: Found: C,38.31; H,1.57; N,4.60. $C_{10}H_5Br_2NO$, Requires: C,38.13; H,1.60; N,4.45%.

(iii) 3-Bromo-2-(1-imidazolylmethyl)benzofuran-5-carbonitrile

Treatment of 3-bromo-2-bromomethylbenzofuran-5-carbonitrile with imidazole and sodium bicarbonate by the method of Example 4(iv) gave 3-bromo-2-(1-imidazolylmethyl)benzofuran-5-carbonitrile, m.p. 119°-122° (from ethyl acetate/petrol, b.p. 80°-100°).

Analysis: Found: C,51.59; H,2.69; N,14.09. $C_{13}H_8BrN_3O$, Requires: C,51.68; H,2.67; N,13.91%.

(iv) 3-Bromo-2-(1-imidazolylmethyl)benzofuran-5-carboxylic acid

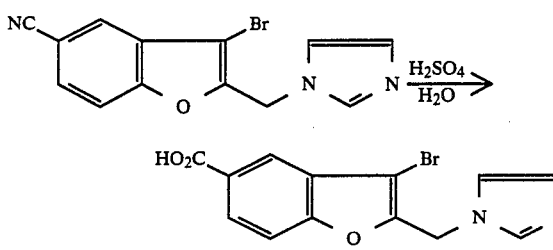

Treatment of 3-bromo-2-(imidazolylmethyl)benzofuran-5-carbonitrile with sulphuric acid/water (1:1) according to the method of Example 16(iv) gave 3-bromo-2-(1-imidazolylmethyl)benzofuran-5-carboxylic acid, m.p. 249°–251°.

Analysis: Found: C,48.58; H,2.80; N,8.72. $C_{13}H_{19}BrN_2O_3$, Requires: C,48.62; H,2.83; N,8.72%.

EXAMPLE 18

3-[1-Imidazolylmethyl]-2-methylbenzo[b]thiophene-7-carboxylic acid methyl ester (i) 2-Methylbenzo[b]thiophene-7-carboxylic acid methyl ester A solution of 2-methylbenzo[b]thiophene-7-carboxylic acid (5.1 g) in methanol (100 ml) was saturated with hydrogen chloride and then heated under reflux for 18 hours. The solution was evaporated and the residue was dissolved in ether. The ether solution was washed with sodium carbonate solution and dried (Na$_2$SO$_4$). Evaporation of the ether gave 2-methylbenzo[b]thiophene-7-carboxylic acid methyl ester (4.7 g), m.p. 48°–49°.

(ii) 3-Chloromethyl-2-methylbenzo[b]thiophene-7-carboxylic acid methyl ester

Hydrogen chloride gas was passed for 30 minutes through a stirred mixture of 2-methylbenzo[b]thiophene-7-carboxylic acid methyl ester (4.50 g), paraformaldehyde (1.23 g) and anhydrous zinc chloride (1.03 g) in chloroform (50 ml). The mixture was stirred at room temperature for 5 hours and then allowed to stand for 18 hours. The mixture was then washed several times with water and the organic layer was dried (Na$_2$SO$_4$) and evaporated. The residue was crystallised from chloroform/petrol (b.p. 60°–80°) to give 3-chloromethyl-2-methylbenzo[b]thiophene-7-carboxylic acid methyl ester (4.10 g), m.p. 125°–126°.

(iii) 3-[1-Imidazolylmethyl]-2-methylbenzo[b]thiophene-7-carboxylic acid methyl ester

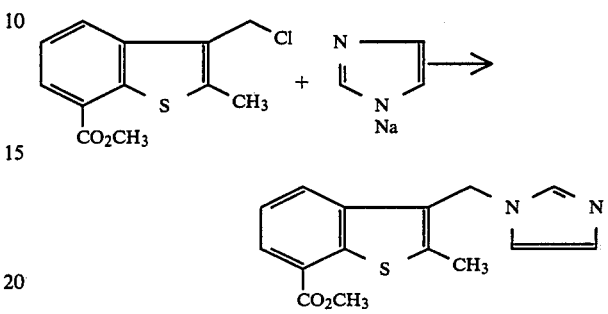

Successive treatment of imidazole with sodium hydride and 3-chloromethyl-2-methylbenzo[b]thiophene-7-carboxylic acid methyl ester in N,N-dimethylformamide by the method of Example 1(ii) gave 3-[1-imidazolylmethyl]-2-methylbenzo[b]thiophene-7-carboxylic acid methyl ester, m.p. 148°–149°.

Analysis: Found: C,62.60; H,4.90; N,9.72. $C_{15}H_{14}N_2O_2S$, Requires: C,62.91; H,4.93; N,9.79%.

EXAMPLE 19

2-(3-Pyridyloxymethyl)-3-methylbenzo[b]thiophene-5-carboxylic acid ethyl ester

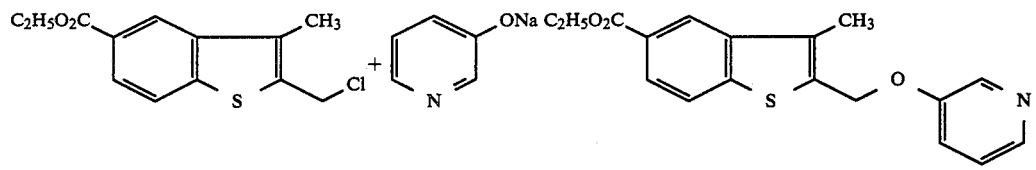

Successive treatment of 3-hydroxypyridine with sodium hydride and 2-chloromethyl-3-methylbenzo[b]thiophene-5-carboxylic acid ethyl ester (the product of Example 1(i)) in N,N-dimethylformamide by the method of Example 3(iv) gave 2-(3-pyridyloxymethyl)-3-methylbenzo[b]thiophene-5-carboxylic acid ethyl ester, m.p. 107°–108° (from ethyl acetate/petrol, b.p. 60°–80°).

Analysis: Found: C,66.01; H,5.22; N,4.35. $C_{18}H_{17}NO_3S$, Requires: C,66.03; H,5.24; N,4.28%.

EXAMPLE 20

E-2-[2-(3-Pyridyl)vinyl]-3-methylbenzo[b]thiophene-5-carboxylic acid ethyl ester

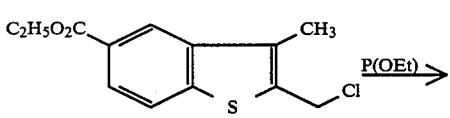

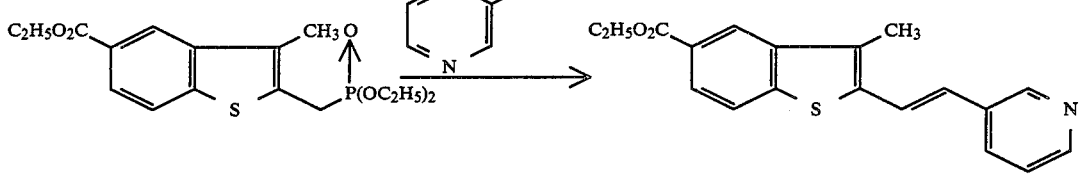

A mixture of 2-chloromethyl-3-methylbenzo[b]thiophene-5-carboxylic acid ethyl ester, prepared as described in Example 1(i), (2.69 g), and triethyl phosphite (3.0 ml) was heated under reflux for 3 hours and then the excess of triethyl phosphite was distilled off. The residue was dissolved in dry 1,2-dimethoxyethane (70 ml) and sodium hydride (0.53 g of a 50% dispersion in mineral oil) was added portionwise with stirring. The mixture was stirred at room temperature for 1 hour and then pyridine-3-carboxaldehyde (1.07 g) was added. The resulting mixture was stirred for 5 hours, allowed to stand for 18 hours and then evaporated to dryness. The residue was chromatographed on silica gel. Elution with chloroform first gave mineral oil and a trace of impurity followed by pure product. Evaporation of the product-containing fractions gave a solid which was crystallised from ether to give E-2-[2-(3-pyridyl)vinyl]-3-methylbenzo[b]thiophene-5-carboxylic acid ethyl ester (1.0 g), m.p. 123°–124°.

Analysis: Found: C,70.43; H,5.29; N,4.16. $C_{19}H_{17}NO_2S$, Requires: C,70.56; H,5.30; N,4.33%.

EXAMPLE 21

3-(3-Pyridyloxymethyl)-2-methylbenzo[b]thiophene-7-carboxylic acid methyl ester

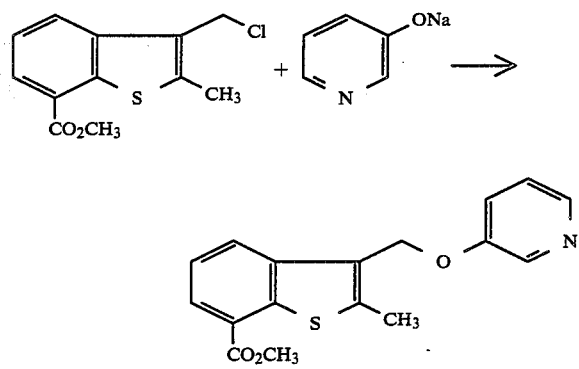

Successive treatment of 3-hydroxypyridine with sodium hydride and 3-chloromethyl-2-methylbenzo[b]thiophene-7-carboxylic acid methyl ester (the product of Example 18(ii)) in N,N-dimethylformamide by the method of Example 3(iv) gave 3-(3-pyridyloxymethyl)-3-methylbenzo[b]thiophene-7-carboxylic acid methyl ester, m.p. 134°–135°. The product was not characterised further.

EXAMPLE 22

2-[1-Imidazolylmethyl]-3-methylindole-5-carboxylic acid (i) 1-Acetyl-2,3-dimethylindole-5-carboxylic acid ethyl ester Sodium hydride (0.8 g of 50% dispersion in mineral oil) was added portionwise to a stirred solution of 2,3-dimethylindole-5-carboxylic acid ethyl ester (3.50 g) in dry N,N-dimethylformamide (25 ml) and the mixture was stirred at room temperature for 30 minutes and then cooled to 0°. A solution of acetyl chloride (1.27 g) in dry N,N-dimethylformamide (2.5 ml) was added dropwise with stirring over 2 minutes. The resulting mixture was stirred at room temperature for 3 hours and then poured into water. The mixture was extracted several times with ethyl acetate and the combined extracts were washed well with water and dried ($Na_2SO_4$). Evaporation of the solvent gave an oil which was chromatographed on silica gel. Elution with chloroform first gave mineral oil followed by product. Evaporation of the product-containing fractions gave a solid which was crystallised from ethyl acetate/petrol (b.p. 60°–80°) to give 1-acetyl-2,3-dimethylindole-5-carboxylic acid ethyl ester (1.22 g), m.p. 98°–101°.

Analysis: Found: C,70.05; H,6.68; N,5.43. $C_{15}H_{17}NO_3$, Requires: C,69.48; H,6.61; N,5.40%.

(ii)
1-Acetyl-2-bromomethyl-3-methylindole-5-carboxylic acid ethyl ester

Bromine (0.40 g) was added dropwise over 1 minute to a stirred solution of 1-acetyl-2,3-dimethylindole-5-carboxylic acid ethyl ester (0.65 g) in acetic acid (1.3 ml). After a few minutes a solid precipitated. The mixture was diluted with ca 5 ml. of ether and the solid was filtered off, washed with ether and dried to give 1-acetyl-2-bromomethyl-3-methylindole-5-carboxylic acid ethyl ester (0.38 g), m.p. 125°–130°. The product was unstable and was used directly in the next stage.

(iii)
1-Acetyl-2-[1-imidazolylmethyl]-3-methylindole-5-carboxylic acid ethyl ester A mixture of 1-acetyl-2-bromomethyl-3-methylindole-5-carboxylic acid ethyl ester (5.74 g), imidazole (11.56 g), sodium bicarbonate (2.9 g) and acetone was stirred for 18 hours and then evaporated. The residue was partitioned between water and ethyl acetate. The ethyl acetate layer was separated, washed with water and dried ($Na_2SO_4$). The solvent was evaporated and the residue was chromatograhed on silica gel. Elution with chloroform first gave some impurity followed by pure product. Evaporation of the product-containing fractions gave 1-acetyl-2-[1-imidazolylmethyl]-3-methylindole-5-carboxylic acid ethyl ester (4.80 g) which was used without further characterisation.

(iv)
2-[1-Imidazolylmethyl]-3-methylindole-5-carboxylic acid

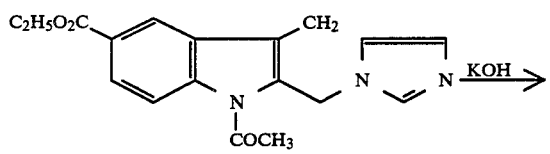

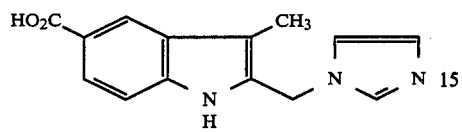

A mixture of 1-acetyl-2-[1-imidazolymethyl]-3-methylindole-5-carboxylic acid ethyl ester (0.143 g), potassium hydroxide (0.15 g), methanol (2 ml) and water (2 ml) was heated under reflux for 3 hours and then evaporated. The residue was dissolved in water and the solution was made just acidic with acetic acid. A gummy solid was formed which was filtered off and dissolved in dilute potassium hydroxide solution. The solution was filtered and the filtrate was made just acidic with acetic acid. The solid was filtered off, washed with water and dried to give 2-[1-imidazolylmethyl]-3-methylindole-5-carboxylic acid (0.077 g), m.p. 268°–269°.

Analysis: Found: C,66.00; H,5.18; N,16.57. $C_{14}H_{13}N_3O_2$, Requires: C,65.87; H,5.13; N,16.46%.

EXAMPLE 23
2-[1-Imidazolylmethyl]-3-methylindole-5-carboxylic acid ethyl ester

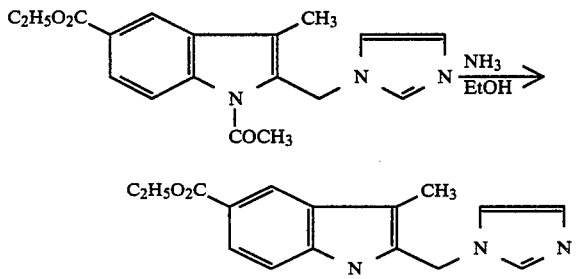

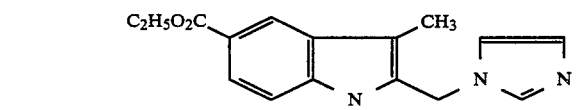

A solution of 1-acetyl-2-[1-imidazolymethyl]-3-methylindole-5-carboxylic acid ethyl ester, prepared as described in Example 22(iii) (4.0 g) in 10% ethanolic ammonia solution was allowed to stand for 18 hours and then evaporated. The residue was crystallised from ethyl acetate to give 2-[1-imidazolylmethyl]-3-methylindole-5-carboxylic acid ethyl ester (2.3 g), m.p. 201°–202°.

Analysis: Found: C,67.70; H.6.04; N,15.03. $C_{16}H_{17}N_3O_2$, Requires: C,67.82; H,6.05; N,14.83%.

EXAMPLE 24
1,3-Dimethyl-2-[1-imidazolylmethyl]indole-5-carboxylic acid ethyl ester

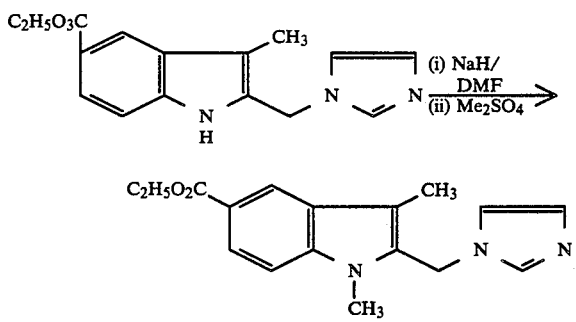

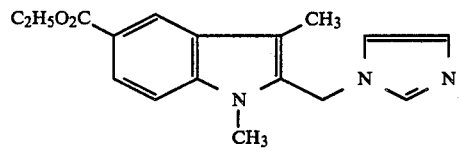

Sodium hydride (0.11 g of 50% dispersion in mineral oil) was added portionwise to a stirred solution of 2-[1-imidazolylmethyl]-3-methylindole-5-carboxylic acid ethyl ester (0.57 g) in dry N,N-dimethylformamide (20 ml) and the mixture was stirred at room temperature for 30 minutes. A solution of dimethyl sulphate (0.26 g) in dry N,N-dimethyl-formamide (2.5 ml) was added dropwise and the mixture was stirred at room temperature for 18 hours and then evaporated. The residue was chromatographed on silica gel. Elution with chloroform first gave mineral oil and impurity followed by pure product. Evaporation of the product-containing fractions gave a solid which was crystallised froml ethyl acetate/petrol (b.p. 60°–80°) to give 1,3-dimethyl-2-[1-imidazolylmethyl]indole-5-carboxylic acid ethyl ester (0.40 g), m.p. 109°–110°.

Analysis: Found: C,68.72; H,6.31; N,14.00. $C_{17}H_{19}N_3O_2$, Requires: C,68.66; H,6.44; N,14.13%.

EXAMPLES 25–34

Table 1 contains a list of carboxylic acids prepared by hydrolysis of the corresponding esters by the method of Example 3(v).

| EXAMPLE | STRUCTURE | M.P. (°C.) | Analysis |
|---|---|---|---|
| 25 | 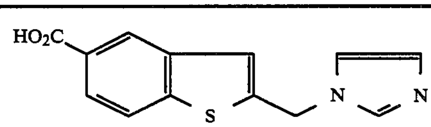 | 280–282 | Found: C,60.25; H,3.83; N,10.88. $C_{13}H_{10}N_2O_2S$ Requires: C,60.45; H,3.90; N,10.85% |
| 26 | 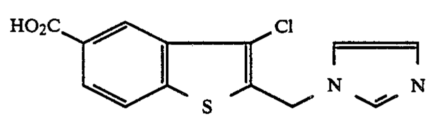 | 265–267 | Found: C,52.96; H,3.05; N,9.55. $C_{13}H_9ClN_2O_2S$ Requires: C,53.33; H,3.10; N,9.51% |

-continued

| EXAMPLE | STRUCTURE | M.P. (°C.) | Analysis |
|---|---|---|---|
| 27 | HO₂C-benzothiophene-3-Br, 2-CH₂-imidazole | 252–253 | Found: C,46.19; H,2.70; N,8.18. $C_{13}H_9BrN_2O_2S$<br>Requires: C,46.31; H,2.69; N,8.31% |
| 28 | HO₂C-benzothiophene-3-SCH₃, 2-CH₂-imidazole | 256–258 | Found: C,54.97; H,4.02; N,9.26. $C_{14}H_{12}N_2O_2S_2$<br>Requires: C,55.24; H,3.98; N,9.21% |
| 29 | benzothiophene with 3-CH₂-imidazole, 2-CH₃, 7-CO₂H | 292–293 | Found: C,61.56; H,4.35; N,10.29. $C_{14}H_{12}N_2O_2S$<br>Requires: C,61.74; H,4.44; N,10.29% |
| 30 | HO₂C-benzothiophene-3-CH₃, 2-CH₂-O-(3-pyridyl) | 220–221$^{(a)}$ | Found: C,63.80; H,4.41; N,4.43. $C_{16}H_{13}NO_3S$<br>Requires: C,64.19; H,4.38; N,4.68% |
| 31 | HO₂C-benzothiophene-3-CH₃, 2-CH=CH-(3-pyridyl) | 338 (d) | Found: C,68.90; H,4.42; N,4.72. $C_{17}H_{13}NO_2S$<br>Requires: C,69.13; H,4.44; N,4.74% |
| 32 | benzothiophene with 3-CH₂-O-(4-pyridyl), 2-CH₃, 7-CO₂H | 298–299 | Found: C,63.36; H,4.67; N,4.41. $C_{16}H_{13}NO_3S$<br>Requires: C,64.19; H,4.38; N,4.68% |
| 33 | HO₂C-benzofuran-3-CH₃, 2-CH₂-imidazole | 237–239 | Found: C,65.38; H,4.82; N,10.92. $C_{14}H_{12}N_2O_3$<br>Requires: C,65.62; H,4.72; N,10.93% |
| 34 | HO₂C-indole(N-CH₃)-3-CH₃, 2-CH₂-imidazole | 277–278$^{(b)}$ | Found: C,66.74; H,5.72; N,15.61. $C_{15}H_{15}N_3O_2$<br>Requires: C,66.90; H,5.61; N,15.61% |

$^{(a)}$RECRYSTALLISED FROM ETHANOL
$^{(b)}$RECRYSTALLISED FROM METHANOL

EXAMPLE 35

1-Methyl-2-(3-pyridylmethyl)naphthalene-7-carboxylic acid (i) 7-Bromo-2-(3-pyridylmethylene)-1-tetralone A mixture of 7-bromo-1-tetralone (11.25 g), pyridin-3-carboxaldehyde (5.35 g), acetic acid (5 ml) and piperidine (6 ml) was heated on a steam bath for 6 hours and then allowed to stand for 18 hours. The volatile material was evaporated and the residue was dissolved in ethyl acetate. The solution was extracted several times with dilute hydrochloric acid and the combined extracts were made just alkaline with dilute sodium hydroxide solution. The solid was filtered off, washed with water and crystallised from methanol to give 7-bromo-2-(3-pyridylmethylene)-1-tetralone (12.8 g), m.p. 124°–125°.

Analysis: Found: C,60.87; H,3.86; N,4.46. $C_{16}H_{12}BrNO$, Requires: C,61.16; H,3.85; N,4.46%.

(ii) 7-Bromo-2-(3-pyridylmethyl)-1-tetralone

A solution of 7-bromo-2-(3-pyridylmethylene)-1-tetralone (13.9 g) in ethanol (150 ml) containing 5% palladium on charcoal (0.50 g) was hydrogenated at 25° and 4 atm. pressure until the theoretical quantity of hydrogen had been taken up. The catalyst was filtered off and the filtrate was evaporated. The residue was distilled to give an oil (12.0 g), b.p. 200°–240° at 1.0 mm containing ca 40% of debrominated material. The product was purified by high pressure liquid chromatography using a silica gel column and a mixture of hexane and ethyl acetate (45:55) as eluent. Debrominated product was eluted first followed by pure 7-bromo-2-(3-pyridylmethyl)-1-tetralone, m.p. 63°–67°.

(iii) 7-Bromo-1-hydroxy-1-methyl-2-(3-pyridylmethyl)-1,2,3,4-tetrahydronaphthalene Methyl magnesium bromide (15 ml of a 3M solution in ether) was added dropwise over 5 minutes to a stirred solution of 7-bromo-2-(3-pyridylmethyl)-1-tetralone (3.20 g) in dry tetrahydrofuran (50 ml). The resulting mixture was heated under reflux with stirring for 10 hours and then cooled. An excess of aqueous ammonium chloride solution was added and the mixture was extracted several times with ether. The combined ethereal extracts were dried ($Na_2SO_4$) and evaporated. The residue was chromatographed on silica gel. Elution with chloroform gave 7-bromo-1-hydroxy-1-methyl-2-(3-pyridylmethyl)-1,2,3,4-tetrahydronaphthalene (2.87 g) as a mixture of isomers which was used directly in the next stage.

(iv) 7-Bromo-1-methyl-2-(3-pyridylmethyl)naphthalene

7-Bromo-1-hydroxy-1-methyl-2-(3-pyridylmethyl)-1,2,3,4-tetrahydronaphthalene (2.87 g) was dissolved in formic acid (30 ml) and the solution was allowed to stand at 25° C. for 6 hours and then evaporated at 35°. The residue was dissolved in ethyl acetate and the solution was washed with sodium bicarbonate solution, water and dried ($Na_2SO_4$). Evaporation of the solvent gave an oil which was chromatographed on silica gel. Elution with chloroform gave the dehydration product as an oil (2.11 g).

A mixture of the oil (2.00 g) and sulphur (0.35 g) was heated at 200° for 2 hours and then cooled. The residue was taken up in a few ml. of ethyl acetate and the mixture was filtered. The filtate was evaporated and the residue was chromatographed on silica gel. Elution with chloroform first gave some impurity followed by pure product. Evaporation of the product-containing fractions gave a solid which was crystallised from petrol (b.p. 80°–100°) to give 7-bromo-1-methyl-2-(3-pyridylmethyl)naphthalene (1.42 g), m.p. 101°–104°.

Analysis: Found: C,65.52; H,4.60; N,4.42. $C_{17}H_{14}BrN$, Requires: C,65.40; H,4.52; N,4.49%.

(v) 1-Methyl-2-(3-pyridylmethyl)naphthalene-7-carbonitrile

Treatment of 7-bromo-1-methyl-2-(3-pyridylmethyl)naphthalene with cuprous cyanide according to the method of Example 8(iv) gave 1-methyl-2-(3-pyridylmethyl)naphthalene-7-carbonitrile, m.p. 110°–112° (from petrol, b.p. 80°–100°).

Analysis: Found: C,84.05; H,5.56; N,10.93. $C_{18}H_{14}N_2$, Requires: C,83.69; H,5.46; N,10.84%.

(vi) 1-Methyl-2-(3-pyridylmethyl)naphthalene-7-carboxylic acid

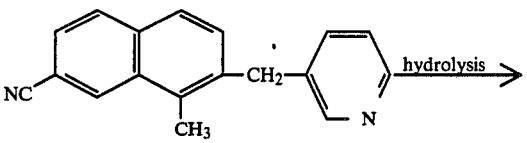
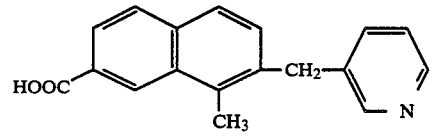

Hydrolysis of 1-methyl-2-(3-pyridylmethyl)naphthalene-7-carbonitrile by the method of Example 8(v) gave 1-methyl-2-(3-pyridylmethyl)naphthalene-7-carboxylic acid, m.p. 210°–211°.

Analysis: Found: C,77.95; H,5.47; N,5.38. $C_{18}H_{15}NO_2$, Requires: C,77.96; H,5.45; N,5.05%.

EXAMPLE 36

3-Chloro-2-(1-imidazolylmethyl)benzo[b]thiophene-6-carboxylic acid

(i) 6-Bromo-3-chlorobenzo[b]thiophene-2-carboxylic acid chloride

A mixture of para-bromocinnamic acid (49.95 g), thionyl chloride (79.80 ml), pyridine (1.77 ml) and chlorobenzene (220 ml) was heated under reflux for 72 hours and then cooled and filtered. The filtrate was evaporated and the residue was triturated with petrol. The solid was filtered off and crystallised from toluene/petrol to give 6-bromo-3-chlorobenzo[b]thiophene-2-carboxylic acid chloride (26.6 g), m.p. 126°–127°.

Analysis: Found: C,35.00; H,1.15. $C_9H_3BrCl_2OS$, Requires: C,34.87; H,0.98%.

(ii) 6-Bromo-3-chloro-2-hydroxymethylbenzo[b]thiophene

A solution of 6-bromo-3-chlorobenzo[b]thiophene-2-carboxylic acid chloride (6.20 g) in dry ether (50 ml) and dry tetrahydrofuran (50 ml) was added dropwise to a stirred suspension of lithium aluminium hydride (0.58 g) in dry ether (250 ml) at 0° under an atmosphere of dry nitrogen. The mixture was stirred at room temperature for 30 minutes and then at reflux for 2½ hours before being cooled and allowed to stand for 18 hours. It was then cooled and the excess of lithium aluminium hydride was decomposed by the cautious addition of water (1.0 ml) followed by 5N sodium hydroxide (1.0 ml) followed by water (2.0 ml) with vigorous stirring. The mixture was filtered and the filtrate was evaporated to give a solid which was chromatographed on silica gel. Elution with chloroform first gave some impurity followed by pure product. The product containing fractions were combined and evaporated to give a solid which was crystallised from chloroform to give 6-bromo-3-chloro-2-hydroxymethylbenzo[b]thiophene (2.22 g), m.p. 117°–118°.

Analysis: Found: C,39.03; H,2.18. $C_9H_6BrClOS$, Requires: C,38.94; H,2.19%.

(iii) 6-Bromo-3-chloro-2-chloromethylbenzo[b]thiophene

Treatment of 6-bromo-3-chloro-2-hydroxymethylbenzo[b]thiophene with thionyl chloride and pyridine by the method of Example 8(ii) gave 6-bromo-3-chloro-2-chloromethylbenzo[b]thiophene, m.p. 95°–96° (from petrol, b.p. 40°–60°).

Analysis: Found: C, 36.12; H, 1.66. $C_9H_5BrCl_2S$, Requires: C, 36.52; H, 1.70%.

(iv) 6-Bromo-3-chloro-2-(1-imidazolylmethyl)benzo[b]thiophene

Treatment of 6-bromo-3-chloro-2-chloromethylbenzo[b]thiophene with imidazole and sodium bicarbonate by the method of Example 4(iv) gave 6-bromo-3-chloro-2-(1-imidazolylmethyl)benzo[b]thiophene, m.p. 123°–124° (from ethyl acetate/petrol).

Analysis: Found: C, 43.99; H, 2.46; N, 8.55. $C_{12}H_8BrClNS$, Requires: C, 44.18; H, 2.47; N, 8.72%.

(v) 3-Chloro-2-(1-imidazolylmethyl)benzo[b]thiophene-6-carbonitrile

Treatment of 6-bromo-3-chloro-2-(1-imidazolylmethyl)benzo[b]thiophene with cuprous cyanide according to the method of Example 8(iv) gave 3-chloro-2-(1-imidazolylmethyl)benzo[b]thiophene-6-carbonitrile, m.p. 158°–159°.

Analysis: Found: C, 56.63; H, 2.97; N, 15.03. $C_{13}H_8ClN_3S$, Requires: C, 57.04; H, 2.95; N, 15.35%.

(vi) 3-Chloro-2-(1-imidazolylmethyl)benzo[b]thiophene-6-carboxylic acid

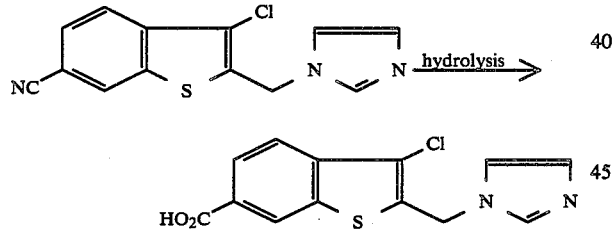

Hydrolysis of 3-chloro-2-(1-imidazolylmethyl)benzo[b]thiophene-6-carbonitrile by the method of Example 16(iv) gave 3-chloro-2-(1-imidazolylmethyl)benzo[b]thiophene-6-carboxylic acid, m.p. 256°–257°.

Analysis: Found: C, 53.24; H, 3.15; N, 9.70. $C_{13}H_9ClN_2O_2S$, Requires: C, 53.33; H, 3.10; N, 9.57%.

EXAMPLE 37

2-(3-Pyridylmethyl)benzofuran-5-carboxylic acid

(i) 5-Bromobenzofuran-2-yl pyrid-3-yl ketone

A mixture of 5-bromosalicylaldehyde (17.7 g), 3-bromoacetylpyridine hydrobromide (25.3 g) and anhydrous potassium carbonate (60.8 g), in 2-butanone (200 ml) was heated under reflux with stirring for 5 hours. The mixture was filtered and the solid was washed with 2-butanone. The combined filtrate and washings were evaporated and the residue was crystallised from methanol to give 5-bromobenzofuran-2-yl pyrid-3-yl ketone (19.2 g), m.p. 144°–145°.

Analysis: Found: C, 55.56; H, 2.79; N, 4.72. $C_{14}H_8BrNO_2$, Requires: C, 55.65; H, 2.67; N, 4.63%.

(ii) 5-Bromo-3-(3-pyridylmethyl)benzofuran

Reduction of 5-bromobenzofuran-2-yl pyrid-3-yl ketone by the method of Example 14(ii) gave 5-bromo-2-(3-pyridylmethyl)benzofuran, m.p. 72°–74° (from petrol, b.p. 60°–80°).

Analysis: Found: C, 58.01; H, 3.51; N, 5.09. $C_{14}H_{10}BrNO$, Requires: C, 58.35; H, 3.50; N, 4.86%.

(iii) 2-(3-Pyridylmethyl)benzofuran-5-carbonitrile

Treatment of 5-bromo-2-(3-pyridylmethyl)benzofuran with cuprous cyanide by the method of Example 8(iv) gave 2-(3-pyridylmethyl)benzofuran-5-carbonitrile, m.p. 59°–61°.

Analysis: Found: C, 76.44; H, 4.27; N, 12.38. $C_{15}H_{10}N_2O$, Requires: C, 76.90; H, 4.28; N, 11.96%.

(iv) 2-(3-Pyridylmethyl)benzofuran-5-carboxylic acid

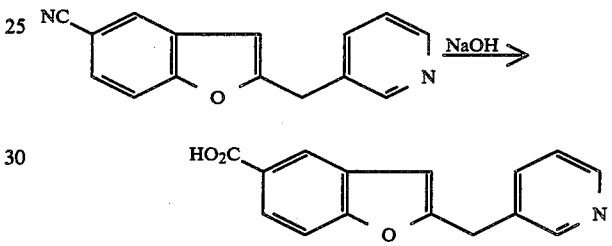

Hydrolysis of 2-(3-pyridylmethyl)benzofuran-5-carbonitrile by the method of Example 8(v) gave 2-(3-pyridylmethyl)benzofuran-5-carboxylic acid, m.p. 197°–198°.

Analysis: Found: C, 71.31; H, 4.51; N, 5.58. $C_{15}H_{11}NO_3$, Requires: C, 71.13; H, 4.38; N, 5.52%.

EXAMPLE 38

5-Carboxy-3-methylbenzo[b]thien-2-yl pyrid-3-yl ketone

(i) 5-Cyano-3-methylbenzo[b]thien-2-yl pyrid-3-yl ketone

Treatment of 5-bromo-3-methylbenzo[b]thien-2-yl pyrid-3-yl ketone (the product of Example 9(i) with cuprous cyanide according to the method of Example 8(iv) gave 5-cyano-3-methylbenzo[b]thien-2-yl pyrid-3-yl ketone, m.p. 138°–139° (from ethyl acetate/petrol, b.p. 60°–80°).

Analysis: Found: C, 69.08; H, 3.70; N, 9.87. $C_{16}H_{10}N_2OS$, Requires: C, 69.04; H, 3.62; N, 10.07%.

(ii) 5-Carboxy-3-methylbenzo[b]thien-2-yl pyrid-3-yl ketone

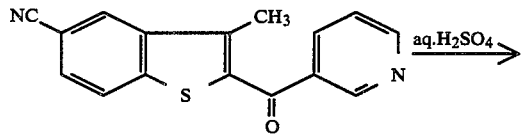

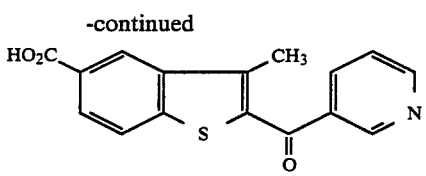

Hydrolysis of 5-cyano-3-methylbenzo[b]thien-2-yl pyrid-3-yl ketone by the method of Example 16(iv) gave 5-carboxy-3-methylbenzo[b]thien-2-yl pyrid-3-yl ketone, m.p. 264°–265°.

Analysis: Found: C, 64.00; H, 3.81; N, 4.60. $C_{16}H_{11}NO_3S$, Requires: C, 64.63; H, 3.73; N, 4.71%.

EXAMPLE 39

3-Ethyl-2-(1-imidazolylmethyl)benzofuran-5-carboxylic acid (i) 5-Bromo-3-ethylbenzofuran-2-carbonitrile A mixture of 5-bromo-2-hydroxypropiophenone (13.74 g) chloroacetonitrile (4.62 ml) and anhydrous potassium carbonate (49.8 g) in dry N,N-dimethylformamide (140 ml) was heated under reflux with stirring for 1 hour. The solvent was evaporated and the residue was partitioned between water and ether. The layers were separated and the aqueous layer was extracted several times with ether. The combined organic layer and extracts were washed well with water and dried (Na2SO4). Evaporation of the solvent gave a solid which was chromatographed on silica gel. Elution with a mixture of chloroform and petrol (3:1) gave 5-bromo-3-ethylbenzofuran-2-carbonitrile (8.90 g) which had m.p. 68°–69° after crystallisation from methanol/H2O.

Analysis %: Found: C, 53.14; H, 3.24; N, 5.71. $C_{11}H_8BrNO$, Requires: C, 52.83; H, 3.22; N, 5.60%.

(ii) 5-Bromo-3-ethylbenzofuran-2-carboxylic acid

A mixture of 5-bromo-3-ethylbenzofuran-2-carbonitrile (2.00 g), potassium hydroxide (1.00 g), water (10 ml) and ethanol (0.5 ml) was heated under reflux for 48 hours and then the solvent was evaporated. The residue was dissolved in water and the solution was filtered and acidified with 2N hydrochloric acid. The solid was filtered off, washed with water and dried to give 5-bromo-3-ethylbenzofuran-2-carboxylic acid (2.01 g) which had m.p. 240°–242° after crystallisation from methanol/H2O.

Analysis %: Found: C, 49.27; H, 3.51. $C_{11}H_9BrO_3$, Requires: C, 49.10; H, 3.3%.

(iii) 5-Bromo-3-ethyl-2-hydroxymethylbenzofuran

To a stirred solution of 5-bromo-3-ethylbenzofuran-2-carboxylic acid (1.91 g) in dry tetrahydrofuran (70 ml) at 0° C. under an atmosphere of dry nitrogen was added dropwise borane-tetrahydrofuran complex (25 ml of 1M solution). The solution was stirred at 0° C. for 1 hour and then at room temperature for 24 hours. Methanol was added continuously to decompose the excess borane complex and then the solution was evaporated. The residue was dissolved in ether and the solution was washed with water and dried (Na2SO4). Evaporation of the ether gave a solid which was chromatographed on silica gel. Elution with chloroform gave a solid which was crystallised from ethyl acetate/petrol to give 5-bromo-3-ethyl-2-hydroxymethylbenzofuran (1.05 g), m.p. 93°–94°.

Analysis %: Found: C, 51.71; H, 4.36. $C_{11}H_{11}BrO_2$, Requires: C, 51.79; H, 4.35.

(iv) 5-Bromo-2-chloromethyl-3-ethylbenzofuran

Treatment of 5-bromo-3-ethyl-2-hydroxymethylbenzofuran with thionyl chloride and pyridine by the method of Example 8(ii) gave 5-bromo-2-chloromethyl-3-ethylbenzofuran, m.p. 58°–60°.

Analysis %: Found: C, 48.41; H, 3.89. $C_{11}H_{10}BrClO$, Requires: C, 48.30; H, 3.68.

(v) 5-Bromo-3-ethyl-2-(1-imidazolylmethyl)benzofuran

Treatment of 5-bromo-3-ethyl-2-hydroxymethylbenzofuran with imidazole and sodium bicarbonate by the method of Example 4(iv) gave 5-bromo-3-ethyl-2-(1-imidazolylmethyl)benzofuran, m.p. 140°–141°.

Analysis %: Found: C,55.10; H,4.29; N,9.18. $C_{14}H_{13}BrN_2O$, Requires: C,55.12; H,4.45; N,9.29.

(vi) 3-Ethyl-2-(1-imidazolylmethyl)benzofuran-5-carbonitrile

Treatment of 5-bromo-3-ethyl-2-(1-imidazolylmethyl)benzofuran with cuprous cyanide according to the method of Example 8(iv) gave 3-ethyl-2-(1-imidazolylmethyl)benzofuran-5-carbonitrile, m.p. 88°–89°.

Analysis %: Found: C,70.99; H,5.28; N,16.46. $C_{15}H_{13}N_3O$, Requires: C,71.70; H,5.21; N,16.72.

(vii) 3-Ethyl-2-(1-imidazolylmethyl)benzofuran-5-carboxylic acid

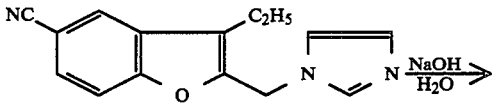
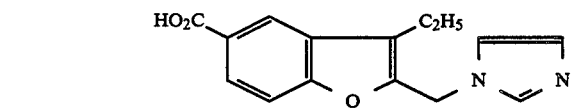

Hydrolysis of 3-ethyl-2-(1-imidazolylmethyl)benzofuran-5-carbonitrile by the method of Example 8(v) gave 3-ethyl-2-(1-imidazolylmethyl)benzofuran-5-carboxylic acid, m.p. 215°–217°.

Analysis %: Found: C,66.05; H,5.29; N,10.31. $C_{15}H_{14}N_2O_3$, Requires: C,66.66; H,5.22; N,10.36.

EXAMPLE 40

2-(1-Imidazolylmethyl)naphthalene-6-carboxylic acid (i) 2-Bromomethylnaphthalene-6-carboxylic acid methyl ester Treatment of 2-methylnaphthalene-6-carboxylic acid methyl ester with N-bromosuccinimide and azobisisobutyronitrile in carbon tetrachloride by the method of Example 3(iii) gave 2-bromomethylnaphthalene-6-carboxylic acid methyl ester, m.p. 103°–106°.

Analysis %: Found: C,55.45; H,4.02. $C_{13}H_{11}BrO_2$, Requires: C,55.93; H,3.97.

(ii) 2-(1-Imidazolylmethyl)naphthalene-6-carboxylic acid methyl ester

Successive treatment of imidazole with sodium hydride and 2-bromomethylnaphthalene-6-carboxylic acid methyl ester in N,N-dimethylformamide by the method of Example 1(ii) gave 2-(1-imidazolylmethyl)naphthalene-6-carboxylic acid methyl ester, m.p. 148°–149°.

Analysis %: Found: C,71.79; H,5.31; N,10.50. $C_{16}H_{14}N_2O_2$, Requires: C,72.16; H,5.30; N,10.52.

(iii) 2-(1-Imidazolylmethyl)naphthalene-6-carboxylic acid

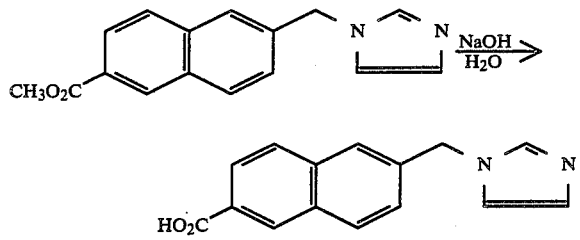

Hydrolysis of 2-(1-imidazolylmethyl)naphthalene-6-carboxylic acid methyl ester by the method of Example 3(v) gave 2-(1-imidazolylmethyl)naphthalene-6-carboxylic acid, m.p. 275°–278°.

Analysis %: Found: C,71.36; H,4.84; N,10.84. $C_{15}H_{12}N_2O_2$, Requires: C,71.41; H,4.79; N,11.10.

EXAMPLE 41

2-(1-Imidazolylmethyl)-1-methylnaphthalene-7-carboxylic acid (i) 7-Bromo-2-dimethylaminomethyl-1-tetralone A mixture of 7-bromo-1-tetralone (4.50 g), dimethylamine hydrochloride (2.50 g), paraformaldehyde (1.0 g), ethanol (6 ml) and concentrated hydrochloric acid (4 drops) was heated under reflux for two hours and cooled. The mixture was diluted with a few ml. of acetone and the solid was filtered off, washed with a little acetone and dried to give 7-bromo-2-dimethylaminomethyl-1-tetralone hydrochloride, m.p. 169°–171°, pure enough for further reaction.

A sample crystallised from methanol/ethyl acetate had m.p. 176°–178°.

Analysis %: Found: C,48.99; H,5.26; N,4.72. $C_{13}H_{16}BrNO·HCl$, Requires: C,49.00; H,5.38; N,4.40.

The hydrochloride was converted to the free base by dissolving in a small volume of water and adding a slight excess of a saturated aqueous solution of sodium bicarbonate. Ether extraction gave the free base as an oil.

(ii) 7-Bromo-2-(1-imidazolylmethyl)-1-tetralone

A solution of 7-bromo-2-dimethylaminomethyl-1-tetralone free base (6.0 g) and imidazole (2.5 g) in xylene (30 ml) was heated under reflux for 1.5 hours and then evaporated. The residue was dissolved in ether and the solution was washed with water followed by dilute hydrochloric acid. The acid extract was made just alkaline with dilute sodium hydroxide solution. The mixture was extracted with chloroform and the combined chloroform extracts were washed with water and dried ($Na_2SO_4$). Evaporation of the solvent gave a solid which was crystallised from ethyl acetate to give 7-bromo-2-(1-imidazolylmethyl)-1-tetralone, m.p. 129°–131°.

Analysis %: Found: C,54.86; H,4.30; N,9.34. $C_{14}H_{13}BrN_2O$, Requires: C,55.10; H,4.29; N,9.18.

(iii) 7-Bromo-1-hydroxy-1-methyl-2-(1-imidazolylmethyl)-1,2,3,4-tetrahydronaphthalene Treatment of 7-bromo-2-(1-imidazolylmethyl)-1-tetralone with methyl magnesium bromide according to the method of Example 35(iii) gave 7-bromo-1-hydroxy-1-methyl-2-(1-imidazolylmethyl)-1,2,3,4-tetrahydronaphthalene as a mixture of isomers which was used directly in the next stage.

(iv) 7-Bromo-2-(1-imidazolylmethyl)-1-methylnaphthalene

A solution of 7-bromo-1-hydroxy-1-methyl-2-(1-imidazolylmethyl)-1,2,3,4-tetrahydronaphthalene (1.95 g) and triphenylmethanol (2.37 g) in trifluoroacetic acid (30 ml) was heated under reflux for 4 days. An additional 2.37 g of triphenylmethanol was added and the solution was heated under reflux for a further 5 days. The solution was evaporated and the residue was basified with diluted sodium hydroxide solution. The mixture was extracted several times with ethyl acetate and the combined extracts were washed with water and dried ($Na_2SO_4$). Evaporation of the solvent gave an oil which was chromatographed on silica gel. Elution with chloroform first gave triphenylmethane and some triphenylmethanol followed by pure product. The product-containing fractions were evaporated to give 7-bromo-2-(1-imidazolylmethyl)-1-methylnaphthalene (1.38 g). A sample crystallised from ethyl acetate/petrol (b.p. 60°–80°) had m.p. 112°–113°.

Analysis %: Found: C,59.82; H,4.32; N,9.10. $C_{15}H_{13}BrN_2$, Requires: C,59.82; H,4.35; N,9.30.

(v) 2-(1-Imidazolylmethyl)-1-methylnaphthalene-7-carbonitrile

Treatment of 7-bromo-2-(1-imidazolylmethyl)-1-methylnaphthalene with cuprous cyanide according to the method of Example 8(iv) gave 2-(1-imidazolylmethyl)-1-methylnaphthalene-7-carbonitrile, m.p. 141°–143°, pure enough for further reaction.

(vi) 2-(1-Imidazolylmethyl)-1-methylnaphthalene-7-carboxylic acid

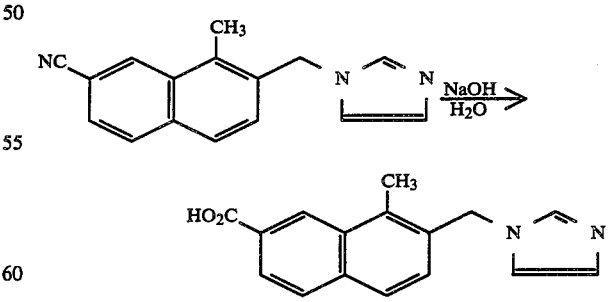

Hydrolysis of 2-(1-imidazolylmethyl)-1-methylnaphthalene-7-carbonitrile by the method of Example 8(v) gave 2-(1-imidazolylmethyl)-1-methylnaphthalene-7-carboxylic acid, m.p. >300°.

Analysis %: Found: C,71.77; H,5.27; N,10.44. $C_{16}H_{14}N_2O_2$, Requires: C,72.17; H,5.30; N,10.52.

| COMPOUND | DOSE (mg/kg i.v.) | % INHIBITION OF TxB$_2$ PRODUCTION POST DOSE | | | | |
|---|---|---|---|---|---|---|
| | | 2 MIN | 15 MIN | 30 MIN | 45 MIN | 75 MIN |
| HO$_2$C—benzothiophene—CH$_2$—imidazole | 0.3 | — | 96 | 89 | — | — |
| HO$_2$C—benzothiophene(CH$_3$)—CH$_2$—imidazole | 0.1 | 100 | 98 | — | 100 | 98 |
| | 0.3 | — | 94 | 95 | — | — |
| HO$_2$C—benzothiophene(Cl)—CH$_2$—imidazole | 0.1 | — | 99 | 96 | — | — |
| | 0.3 | 99 | 100 | — | 100 | 99 |
| HO$_2$C—benzothiophene(SCH$_3$)—CH$_2$—imidazole | 0.1 | — | 93 | 95 | — | — |
| | 0.3 | 99 | 98 | — | 97 | 95 |
| HO$_2$C—benzothiophene(CH$_3$)—CH$_2$—imidazole (isomer) | 0.1 | — | 100 | 100 | — | — |
| | 0.3 | 100 | 100 | — | 100 | 100 |
| HO$_2$C—benzothiophene(CH$_3$)—CH$_2$—pyridine | 0.1 | — | 96 | 85 | — | — |
| | 0.3 | 98 | 99 | — | 97 | 83 |
| HO$_2$C—benzothiophene(CH$_3$)—CH$_2$—pyridine (isomer) | 0.1 | — | 76 | 46 | — | — |
| | 0.3 | 90 | 91 | — | 71 | 52 |
| HO$_2$C—benzothiophene(CH$_3$)—S—pyridine | 0.1 | — | 29 | 22 | — | — |
| | 0.3 | 98 | 81 | — | 36 | 33 |
| HO$_2$C—benzofuran(CH$_3$)—CH$_2$—imidazole | 0.1 | — | 47 | 37 | — | — |
| | 0.3 | 92 | 83 | — | 65 | 51 |
| HO$_2$C—benzofuran(Br)—CH$_2$—imidazole | 0.1 | — | 52 | 33 | — | — |
| | 0.3 | 87 | 84 | — | 65 | 41 |
| HO$_2$C—benzofuran(Cl)—CH$_2$—imidazole | 0.1 | — | 88 | 82 | — | — |
| | 0.3 | 98 | 97 | — | 93 | 86 |
| HO$_2$C—N-methylindole(CH$_3$)—CH$_2$—imidazole | 0.1 | — | 85 | 84 | — | — |
| | 0.3 | 99 | 95 | — | 93 | 81 |

-continued

| COMPOUND | DOSE (mg/kg i.v.) | % INHIBITION OF $TxB_2$ PRODUCTION POST DOSE | | | | |
|---|---|---|---|---|---|---|
| | | 2 MIN | 15 MIN | 30 MIN | 45 MIN | 75 MIN |
| 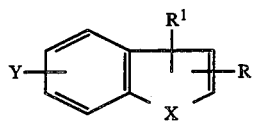 | 0.1 | — | 95 | 92 | — | — |
| | 0.3 | 99 | 98 | — | 95 | 97 |

We claim:

1. A compound of the formula:

$$Y\text{—}\underset{X}{\overset{R^1}{\boxed{\phantom{xxx}}}}\text{—}R$$

or a pharmaceutically acceptable salt thereof, wherein $R^1$ is hydrogen, F, Cl, Br, I, $C_1$-$C_4$ alkyl or —S(-$C_1$-$C_4$ alkyl);
Y is —COOH, —COO($C_1$-$C_4$ alkyl) or —CONH$_2$;
X is —CH=CH—; and
R is 1-imidazolylmethyl or (3-pyridyl)—Z—
wherein Z is —CH$_2$—, —CH=CH—, —OCH$_2$—, —CO— or —S—.

2. A compound as claimed in claim 1 wherein R is 1-imidazolylmethyl or 3-pyridylmethyl, Y is —COOH and $R^1$ is hydrogen or CH$_3$.

3. A compound as claimed in claim 1 wherein R is imidazolylmethyl or 3-pyridylmethyl at the 2-position of the molecule; Y is —COOH at the 6- or 7-position; and $R^1$ is Cl, Br, $C_1$-$C_4$ alkyl or $C_1$-$C_4$ alkylthio at the 1-position of the molecule.

4. A compound as claimed in claim 3 wherein R is 3-pyridylmethyl, Y is —COOH at the 7-position of the molecule and $R^1$ is CH$_3$.

5. A pharmaceutical composition useful for inhibiting the action of the thromboxane synthetase enzyme in an animal without significantly inhibiting the action of the prostacyclin synthetase or cyclo-oxygenase enzymes, said composition comprising a pharmaceutically acceptable carrier and a therapeutically-effective amount of a compound as claimed in claim 1.

6. A method for inhibiting the action of the thromboxane synthetase enzyme in an animal without significantly inhibiting the action of the prostacyclin synthetase or cyclo-oxygenase enzymes, which comprises administering to said animal a thromboxane synthetase enzyme inhibiting amount of a compound as claimed in claim 1.

* * * * *